United States Patent
Baxendale et al.

(10) Patent No.: US 9,796,653 B2
(45) Date of Patent: Oct. 24, 2017

(54) METHODS OF PREPARING α,β-UNSATURATED OR α-HALO KETONES AND ALDEHYDES

(71) Applicant: International Flavors & Fragrances Inc., New York, NY (US)

(72) Inventors: Ian R Baxendale, Durham (GB); James S Sharley, Durham (GB); Amadeo Fernández Miranda, Benicarlo (ES); Ana Maria Collado Pérez, Castellón (ES)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

(21) Appl. No.: 15/382,782

(22) Filed: Dec. 19, 2016

(65) Prior Publication Data
US 2017/0174607 A1     Jun. 22, 2017

(51) Int. Cl.
| | |
|---|---|
| *C07C 67/00* | (2006.01) |
| *C07C 45/00* | (2006.01) |
| *C07C 67/317* | (2006.01) |
| *C07C 45/27* | (2006.01) |

(52) U.S. Cl.
CPC ............ *C07C 67/317* (2013.01); *C07C 45/27* (2013.01); *C07C 67/00* (2013.01); *C07C 2101/08* (2013.01); *C07C 2101/10* (2013.01); *C07C 2101/14* (2013.01); *C07C 2101/16* (2013.01); *C07C 2102/08* (2013.01)

(58) Field of Classification Search
CPC .............................. C07C 67/317; C07C 45/27
USPC ........................................................ 560/121
See application file for complete search history.

(56) References Cited

U.S. PATENT DOCUMENTS 6,586,620 B1     7/2003     Crawford et al.

OTHER PUBLICATIONS

Extended European Search Report dated May 23, 2017 for Application No. EP 16203742.8.
Beat Wi Nter et al : "Further Explorations into the Synthesis of Dehydro-Hedi one", Helv Eti Ca Chimi Ca Acta, vol. 96, No. 2,Feb. 18, 2013 (Feb. 18, 2013), pp. 246-258, XP55365648, CH ISSN: 0018-019X, DOI: 10.1002/hl ca.201200440 p. 246, l i ne 1-p. 251, line 6.
Tatsuya Shono et al : "El ectroorganic chemistry. XXI. Selective formation of .alpha.-acetoxy ketones and general synthesis of 2,3-di substituted 2-cycl opentenones through the anodicoxidation of enolacetates", Journal of the American Chemical Society, vol . 97, No. 21 Oct. 1, 1975 (Oct. 1, 1975) , pp. 6144-6147, XP55365641, ISSN: 0002-7863, DOI: 10.1021/ja00854a030.
David J. Ager et al : "The Conjugate 1-15 Addition of a Silyl Group to Enones and its Removal wi Copper (!!) Bromide: A Protecting Group for the [alpha][beta]-Unsaturation of [alpha][beta]-Unsaturated Ketones", Journal of The Chemical Society, Perkin Transactions I , No. 0, Jan. 1, 1981 (Jan. 1, 1981) , pp. 2520-2526, XP55366066, GB ISSN: 0300-922X, DOI: 10.1039/P19810002520 p. 2520, col. I , l i 1-p. 2522, col. I , l ine 16.

*Primary Examiner* — Sikarl Witherspoon
(74) *Attorney, Agent, or Firm* — Martin Zhang; XuFan Tseng; Elizabeth M. Stover

(57) ABSTRACT

Copper(II) bromide mediated oxidation of acylated enol and use of the reaction in the synthesis of α,β-unsaturated or α-bromo ketones or aldehydes are disclosed. The method provides an efficient and practical process for manufacturing dehydrohedione (DHH) and many other versatile α,β-unsaturated or α-bromo ketones or aldehydes in large scales to avoid using precious metal compounds.

20 Claims, No Drawings ered or α-halo ketones and aldehydes, among others,
METHODS OF PREPARING α,β-UNSATURATED OR α-HALO KETONES AND ALDEHYDES

FIELD OF THE INVENTION

The present invention relates to synthesis of α,β-unsaturated or α-halo ketones and aldehydes, among others, through copper(II) bromide mediated oxidation of enol acetates, in particular a practical process for manufacturing dehydrohedione (DHH), a compound widely used in the fragrance industry.

BACKGROUND OF THE INVENTION

α,β-Unsaturated ketones or aldehydes are important fine chemicals widely used not only in general organic synthesis, such as in Michael additions and Diels-Alder reactions, etc., but also in the cosmetic and personal care industries. For example, Hedione®(methyldihydrojasmonate) is an important fragrance component used in many commercial blends. Preparation of α,β-unsaturated ketones or aldehydes from more readily available simple ketones and aldehydes, respectively, through oxidation of the corresponding enolates is known, for example, through the Saegusa oxidation of enol silyl ether (Ito, Y.; et al., *J. Org. Chem.* 1978, 43, 1011-1013); however, this synthetically important transformation often requires relatively high palladium loadings (e.g., oxidation of trimethylsilyl ether of cyclohexanone to form 2-cyclohexen-1-one requires 0.5 equivalents of Pd(OAc)$_2$), which severely limits its utility in commercial scale syntheses of compounds that would be used for personal care or pharmaceutical industries.

Similarly, α-halo ketones or aldehydes are versatile synthetic building blocks not only because they can serve as precursors to α,β-unsaturated ketones and aldehydes, but they can be converted into many other compounds through nucleophilic substitution of the α-halogen, in particular an α-bromo group. Therefore, synthesis of α-halo, in particular α-bromo, ketones or aldehydes is of great synthetic value.

Although copper(II) halides have been known to effect α-bromination or chlorination of ketones for over half a century (see, e.g., Kosower, E. M.; et al., *J. Org. Chem.* 1963, 28, 633-638; Kosower, E. M.; et al., *J. Org. Chem.* 1963, 28, 630-633; Kochi, J. K., *J. Am. Chem. Soc.* 1955, 77, 5274-5278), oxidation of enol acetates by copper salts have not been reported or used to effect such desired chemical transformations at commercial scales. Because copper(II) salts are inexpensive and abundant and less toxic than precious metals such as palladium, their use in the synthesis of organic compounds, especially those used for personal care and pharmaceutical products, remains underexplored.

SUMMARY OF THE INVENTION

The present application discloses syntheses of α,β-unsaturated or α-bromo ketones and aldehydes via copper(II) bromide-mediated oxidation of acylated enols (e.g., enol acetates), which offers significant cost savings for using copper(II) salts in organic synthesis to replace more expensive precious metal reagents such as palladium(II) complexes. The employment of a copper redox system to effect α-bromination followed by elimination of HBr offers a comparable process to the Saegusa oxidation, such that the use of palladium could be avoided.

In one aspect, the present invention provides a method of preparing an α,β-unsaturated ketone or aldehyde, comprising a reaction of a corresponding acylated enol (e.g., enol acetate) with copper(II) bromide (CuBr$_2$) in the presence or absence of a solvent.

In another aspect, the present invention provides a method of preparing an α-bromo ketone or aldehyde, comprising a reaction of a corresponding acylated enol (e.g., enol acetate) with CuBr$_2$ in the presence or absence of a solvent.

In another aspect, the present invention provides a method of synthesizing phenol derivatives by CuBr$_2$-mediated oxidation of the corresponding cyclohexanone acylated enol (e.g., enol acetate) intermediates.

Other aspects and advantages of the present invention can be better appreciated in view of the detailed description and claims.

DETAILED DESCRIPTION OF THE INVENTION

The present invention is based on surprising discoveries of the versatile utility of inexpensive copper salts, in particular CuBr$_2$, in the synthesis of α,β-unsaturated and/or α-bromo ketones or aldehydes by oxidation/bromination of the corresponding acylated enol (e.g., enol acetate), which in turn can be prepared readily from low-cost starting materials, e.g., simple ketones or aldehydes. The transformations are particularly of interest in the manufacture of industrially important chemicals such as dehydrohedione (DHH) and analogues.

In one aspect, the present invention provides a method of preparing an α,β-unsaturated or α-bromo ketone or aldehyde, comprising oxidation of a corresponding acylated enol (e.g., enol acetate) with CuBr$_2$ in the presence or absence of a solvent.

In another aspect, the present invention provides a method of preparing an α-bromo ketone or aldehyde, comprising oxidation of a corresponding acylated enol (e.g., enol acetate) with CuBr$_2$ in the presence or absence of a solvent.

In one embodiment, the solvent is acetonitrile, lower alkyl alcohols, toluene, tetrahydrofuran, dimethyl sulfoxide, water, or any combinations thereof.

In one preferred embodiment, the solvent is acetonitrile, methanol, ethanol, isopropanol, water, or a combination thereof.

In one preferred embodiment, the reaction is conducted at an elevated temperature.

In another preferred embodiment, the reaction is conducted at a reflux temperature.

In some embodiments, the reaction can be conducted in the presence of a catalytically effective amount of CuBr$_2$ (e.g., at least 0.1, at least 0.5, at least 1, at least 1.5, and at least 2 mole equivalents per mole of the acylated enol), and a stoichiometric or excess amount of a second oxidant including O$_2$ (Air) that can regenerate CuBr$_2$ in situ.

In some preferred embodiments, the reaction can be conducted in the presence of about 2 or more mole equivalents of CuBr$_2$, with a preferred range of 1.5 to 2.5 equivalents CuBr$_2$.

In some embodiments, the reaction can be characterized by equation (A), wherein the α,β-unsaturated ketone or aldehyde has a structure of formula (I), the α-bromo ketone or aldehyde has a structure of formula (II), and the acylated enol has a structure of formula (III):

(A)

(III) → (I) and/or (II)

(B)

(IIIa) → (Ia) and/or (IIa)

wherein:

$R^1$ and $R^2$ are each independently selected from the group consisting of hydrogen, $C_1$-$C_6$ alkyl, $C_6$-$C_{10}$ aryl, arylalkyl, $C_3$-$C_8$ cycloalkyl, and cycloalkylalkyl, each except hydrogen optionally substituted by one or more $R^y$ groups; or alternatively $R^1$ and $R^2$ together form $C_2$-$C_5$ alkylene or 1,2-phenylene, each optionally substituted by one or more $R^y$ groups;

$R^3$ is selected from the group consisting of hydrogen, $C_1$-$C_{10}$ alkyl, $C_6$-$C_{10}$ aryl, arylalkyl, and —$(CH_2)_iCO_2R^z$, wherein i is 1, 2, or 3, and $R^z$ is $C_1$-$C_4$ alkyl;

$R^4$ is selected from the group consisting of hydrogen, $C_1$-$C_6$ alkyl, $C_6$-$C_{10}$ aryl, arylalkyl, and —$(CH_2)_jCO_2R^z$, wherein j is 0, 1, 2, or 3, and $R^z$ is $C_1$-$C_4$ alkyl;

or alternatively $R^3$ and $R^4$ together form a $C_3$-$C_5$ alkylene optionally substituted by one or more $R^y$ groups;

$R^5$ is selected from the group consisting of $C_1$-$C_6$ alkyl, $C_6$-$C_{10}$ aryl, arylalkyl, $C_3$-$C_8$ cycloalkyl, and cycloalkylalkyl; and $R^y$ at each occurrence is independently selected from the group consisting of $C_1$-$C_6$ alkyl, $C_1$-$C_4$ haloalkyl, $C_1$-$C_4$ alkoxy, halo, and —$(CH_2)_kCO_2R^z$, wherein k is 0, 1, 2, or 3, and $R^z$ is $C_1$-$C_4$ alkyl.

In some embodiments, the reaction is characterized by equation (A), wherein:

$R^1$ and $R^2$ together form a $C_2$-$C_3$ alkylene optionally substituted by one or more $R^y$ groups;

$R^y$ at each occurrence is independently selected from the group consisting of halogen, $C_1$-$C_6$ alkyl, $C_1$-$C_4$ haloalkyl, $C_1$-$C_4$ alkoxy, halo, —$(CH_2)_kCO_2R^z$, wherein k is 0, 1, 2, or 3, and $R^z$ is $C_1$-$C_4$ alkyl;

$R^3$ is selected from the group consisting of hydrogen, $C_1$-$C_{10}$ alkyl, and arylalkyl;

$R^4$ is hydrogen, $C_1$-$C_6$ alkyl, $C_6$-$C_{10}$ aryl, arylalkyl, $C_3$-$C_8$ cycloalkyl, cycloalkylalkyl, —$(CH_2)_jCO_2R^z$, wherein j is 1, 2, or 3 and $R^z$ is $C_1$-$C_4$ alkyl; and $R^5$ is methyl;

In some embodiments, the reaction is characterized by equation (A), wherein $R^1$ and $R^2$ together form —$CH_2CH_2$— optionally substituted by one or two $R^y$ groups, further characterized by equation (B):

wherein:

n is 0, 1, or 2;

$R^3$ is hydrogen, $C_1$-$C_{10}$ alkyl, or arylalkyl;

$R^4$ is hydrogen, $C_1$-$C_6$ alkyl, or —$(CH_2)_jCO_2R^z$, wherein j is 1, 2, or 3, and $R^z$ is $C_1$-$C_4$ alkyl;

$R^5$ is $C_1$-$C_6$ alkyl, $C_6$-$C_{10}$ aryl, arylalkyl, $C_3$-$C_8$ cycloalkyl, or cycloalkylalkyl; and $R^y$ at each occurrence is independent selected from the group consisting of $C_1$-$C_6$ alkyl, $C_1$-$C_4$ haloalkyl, $C_1$-$C_4$ alkoxy, halo, and —$(CH_2)_kCO_2R^z$, wherein k is 0, 1, or 2, and $R^z$ is $C_1$-$C_4$ alkyl.

In some embodiments, n is 0; $R^3$ is hydrogen, $C_1$-$C_8$ alkyl, or benzyl; and $R^4$ is hydrogen, $C_1$-$C_4$ alkyl, or —$CH_2CO_2R^z$, wherein $R^z$ is methyl or ethyl; and $R^5$ is methyl.

In some embodiments, the α,β-unsaturated ketone is:

($R^z$ = methyl or ethyl)

In a preferred embodiment, the α,β-unsaturated ketone is dehydrohedione.

In some embodiments, the α-bromo ketone or aldehyde is selected from the group consisting of:

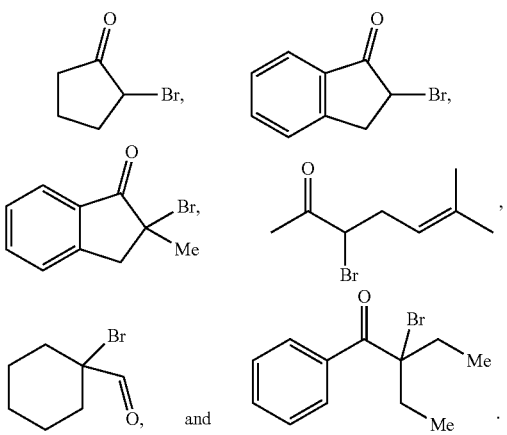

In some embodiments, the method of the present invention further comprises preparing the acylated enol intermediate by reacting a corresponding ketone or aldehyde with an acylating agent in the presence of an acid or base, characterized by equation (C):

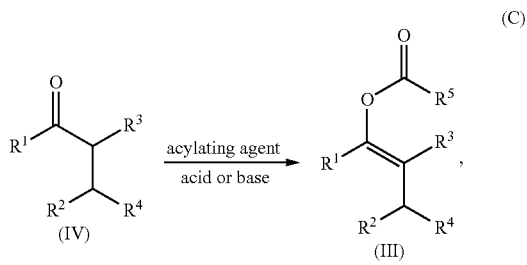

wherein each of $R^1$-$R^5$ is defined above.

In some embodiments, the acylating agent is acetic anhydride, acetyl chloride, or isopropenyl acetate; wherein the acid is an organic acid or a mineral acid; and wherein the base is an organic or inorganic base.

In some embodiments, the acylating agent is acetic anhydride or isopropenyl acetate, and the acid is a catalytic amount of p-toluenesulphonic acid.

In some preferred embodiments, the present invention provides a method of preparing a compound of formula Ib, characterized by equation (D):

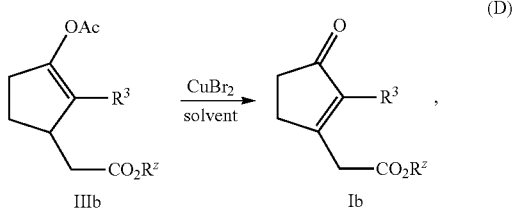

the method comprising reacting an enol acetate intermediate of formula IIIb with at least 1.5 equivalents of $CuBr_2$ in a solvent selected from acetonitrile and lower alkyl alcohols, or a combination thereof, at an elevated temperature until the compound of formula IIIb is substantially consumed; and isolating compound Ib from the reaction mixture, wherein $R^3$ is $C_1$-$C_8$ alkyl, and $R^z$ is $C_1$-$C_4$ alkyl.

In some more preferred embodiments, the enol acetate intermediate IIIb is prepared by reacting a compound of formula IVb with isopropenyl acetate in the presence of p-toluenesulfonic acid (p-TSA), characterized by equation (E):

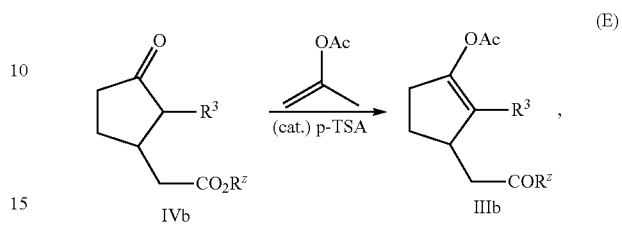

wherein $R^3$ is $C_1$-$C_8$ alkyl, and $R^z$ is $C_1$-$C_4$ alkyl.

In some more preferred embodiments, the amount of p-TSA is about 0.1 to about 0.5 equivalents relative to the compound of IVb.

In some more preferred embodiments, the amount of p-TSA is about 0.2 equivalents relative to the compound of formula IVb.

In some more preferred embodiments, the amount of $CuBr_2$ is about 2 equivalents; wherein the solvent is acetonitrile, methanol, or a combination thereof, and wherein the elevated temperature is reflux temperature.

In some more preferred embodiments, $R^3$ is $C_2$-$C_6$ alkyl, and $R^z$ is methyl or ethyl. In some more preferred embodiments, wherein $R^3$ is 1-pentyl, and $R^z$ is methyl, the amount of $CuBr_2$ is about 2 equivalents, the solvent is acetonitrile or methanol, and the elevated temperature is reflux temperature.

A specifically more preferred embodiment is preparation of dehydrohedione 1b by reacting enol acetate intermediate 1a in Table 2 with about 2 equivalents of $CuBr_2$ in acetonitrile at reflux until the reaction goes to completion and isolating the product 1b.

In some embodiments, the present invention further provides combinations of any of the preferred embodiments disclosed here.

The term "alkyl," as used herein, means a straight or branched-chain saturated hydrocarbon group containing from 1 to 10 carbon atoms, preferably 1 to 8 carbon atoms, sometimes more preferably 1 to 6 carbon atoms ("lower alkyl"), and sometimes more preferably 1 to 4 carbon atoms, which is connected with the rest of the molecular moiety through a single bond. Representative examples of alkyl include, but are not limited to, methyl, ethyl, n-propyl, iso-propyl, n-butyl, sec-butyl, iso-butyl, tert-butyl, etc.

The term "alkoxy," as used herein, means an "—O-alkyl" group, where alkyl is as defined herein. Representative examples of alkoxy include, but are not limited to, methoxy, ethoxy, propoxy, 2-propoxy, butoxy, tert-butoxy, etc.

The term "aryl," as used herein, means an aromatic hydrocarbon group comprised of 6 to 14, preferably 6 to 10, carbon atoms formed from an aromatic hydrocarbon by loss of a hydrogen atom. Representative examples of aryl include, but are not limited to, phenyl and naphthyl. Unless specified in the present application, the term "aryl" may be substituted by one or more substituents, such as $C_1$-$C_6$ alkyl, $C_1$-$C_6$ haloalkyl, $C_1$-$C_6$ alkoxy, etc.

The term "arylalkyl," as used herein, means alkyl group substituted by one or two aryl groups, wherein alkyl and aryl are as defined herein. Examples of arylalkyl include, but are not limited to, benzyl, 2-phenylethyl, diphenylmethyl, and naphth-2-ylmethyl, etc.

The term "carboxyl," as used herein, means a —C(O)O⁻ or —CO$_2$H group.

The term "cycloalkyl," as used herein, means a cyclic hydrocarbon group containing from 3 to 8 carbon atoms, preferably 3 to 6 carbon atoms, where such groups can be saturated or unsaturated, but not aromatic. In certain embodiments, cycloalkyl groups are preferably fully saturated. Examples of cycloalkyl include, but are not limited to, cyclopropyl, cyclobutyl, cyclopentyl, cyclohexyl, cyclohexenyl, etc.

The term "cycloalkylalkyl," as used herein, means alkyl group substituted by at least one, preferably one or two, cycloalkyl group, wherein alkyl and cycloalkyl are as defined herein.

The term "acyl" or "acylated" means —C(O)R$^5$, where R$^5$ is defined above.

The term "halo" or "halogen" refers to F, Cl, Br, and I, preferably Cl or Br.

The term "haloalkyl" refers to an alkyl group substituted by one or more halogen atoms.

The singular forms "a", "an", and "the" include plural reference, and vice versa, unless the context clearly dictates otherwise.

The term "about," when used in front of a number, indicates that the number can fluctuate for ±10%, preferably within ±5%.

While the CuBr$_2$ mediated oxidation is in principle applicable to transformations of a wide range of substrates having enol acetate moiety, as demonstrated in this application, preparation of dehydrohedione (DHH) is used as an illustrative, non-limiting example to demonstrate the industrial utility of the methodology.

Of all the possible isomers of Hedione in Scheme 1, the (1R,2S)-(+)-cis isomer is the most desirable, being almost entirely responsible for the characteristic odor of methyldihydrojasmonate. Whilst enantioselective routes to this compound have been reported, they are prohibitively expensive and poorly scalable, hence, 'cis-enhancement' of Hedione® is still the favored approach within the fragrance industry. This is primarily achieved through hydrogenation of DHH (1b, its α,β-unsaturated analogue). Although several syntheses of DHH have been developed, the preferred method of DHH synthesis on a large scale still remains through direct oxidation of Hedione® (see, e.g., U.S. Pat. No. 6,586,620).

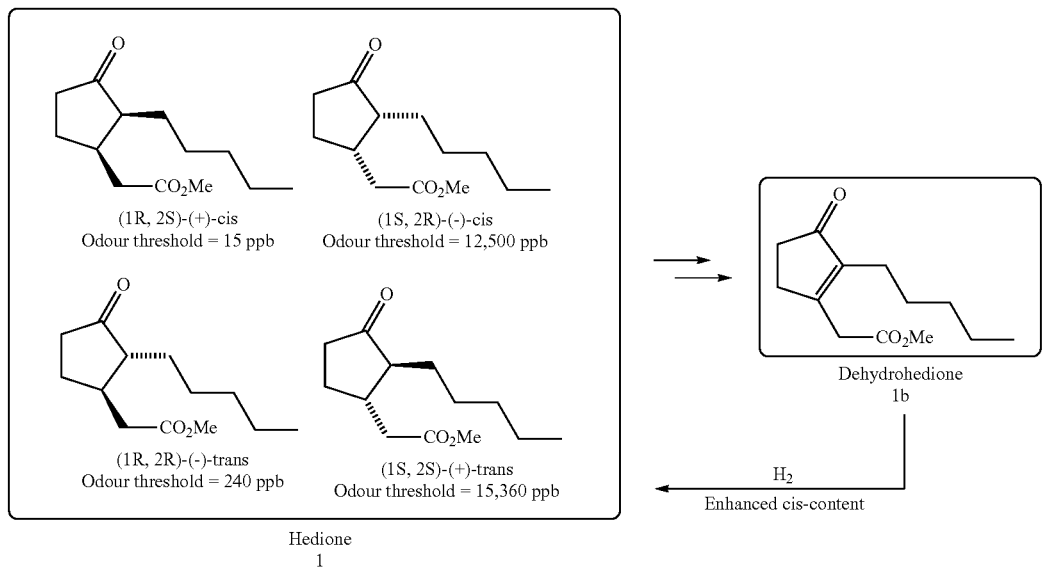

Scheme 1. Methyldihydrojasmonate (1) diastereomer odour thresholds and the general scheme of "cis-enhancement" process Herein, this application discloses a convenient and operationally simple means of effecting the oxidative transformation of acylated enols (e.g., enol acetates) to α,β-unsaturated ketones in a single step using copper(II) bromide, preferably in superstoichiometric amounts.

Initial investigations involved the oxidation of the Hedione® enol acetate (1a), which was regioselectively prepared in order to direct the initial bromination towards the desired more substituted position. This was accomplished in high yield and with excellent selectivity by treatment of the parent ketone with either acetic anhydride or isopropenyl acetate under mildly acidic conditions. The latter reagent was preferred as less of the acetylating agent was required (2 equivalents) and only acetone was generated as a by-product, which could be easily evaporated from the reaction medium. The subsequent oxidation was also achieved under mild conditions with full conversion to the α,β-unsaturated cyclic ketone observed after just 5 minutes at reflux in acetonitrile.

TABLE 1

Screening of reaction conditions

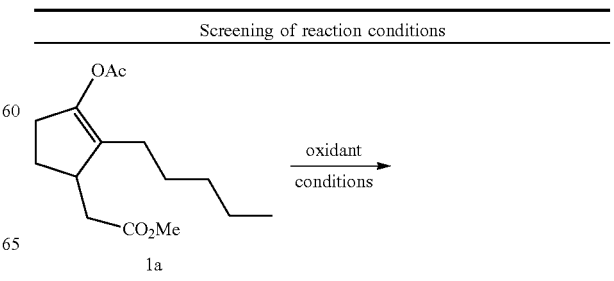

TABLE 1-continued

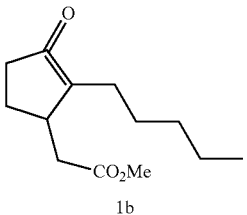

1b

| Entry | Solvent | Oxidant (equivalents) | Time | Consumption[a] (%) | Yield[a] (%) |
|---|---|---|---|---|---|
| 1 | MeCN | CuBr$_2$ (2.0) | 5 min | 100 | 92 |
| 2 | toluene | CuBr$_2$ (2.0) | 30 min | 40 | 0 |
| 3 | MeOH | CuBr$_2$ (2.0) | 30 min | 100 | 64 |
| 4 | CH$_2$Cl$_2$ | CuBr$_2$ (2.0) | 30 min | 66 | 0 |
| 5 | CHCl$_3$ | CuBr$_2$ (2.0) | 30 min | 45 | 0 |
| 6 | THF | CuBr$_2$ (2.0) | 30 min | 23 | 0 |
| 7[b] | DMSO | CuBr$_2$ (2.0) | 30 min | 84 | 0 |
| 8 | MeCN | CuCl$_2$ (2.0) | 18 h | 44 | 0 |
| 9 | MeCN | Cu(OTf)$_2$ (2.0) | 18 h | 0 | 0 |
| 10 | MeCN | Cu(OAc)$_2$ (2.0) | 18 h | 0 | 0 |
| 11 | MeCN | CuBr$_2$ (1.75) | 5 min | 100 | 77 |
| 12 | MeCN | CuBr$_2$ (1.5) | 5 min | 100 | 72 |
| 13 | MeCN | CuBr$_2$ (1.0) | 5 min | 100 | 53 |
| 14 | MeCN | CuBr$_2$ (0.5) | 5 min | 100 | 28 |
| 15[c,d,g] | MeCN | CuBr$_2$ (0.5) | 24 h | 0 | 0 |
| 16[c,e,g] | MeCN | CuBr$_2$ (0.5) | 24 h | 23 | 0 |
| 17[c,f,g] | MeCN | CuBr$_2$ (0.5) | 24 h | 0 | 0 |

Reaction conditions: 1 mmol scale, 0.2 M solution, reflux unless stated otherwise.
Notes:
[a]Yield/starting material consumption quantified using 2-nitrotoluene as an internal $^1$H-NMR standard.
[b]Conducted at 100° C.
[c]Carried out under an O$_2$ atmosphere.
[d]DIPEA (5 equivalents added).
[e]Pyridine (2 equivalents) added.
[f]2,6-di-tert-butylpyridine (2 equivalents) added.
[g]Conducted at room temperature ~20° C.

The above experiments demonstrated the viable method for formation of DHH (1b) from the relevant enol acetate (1a) in high isolated yield (99%) using CuBr$_2$ (2 equivalents) in acetonitrile, at reflux after only 5 minutes. Of the other solvents screened, only methanol gave any appreciable amount of the product. Surprisingly, of the additional copper (II) salts evaluated (chloride, acetate and triflate), none yielded any of the desired product, suggesting the likelihood of bromine transfer to generate an α-brominated intermediate. Reducing the equivalents of CuBr$_2$ was found to be detrimental to the yield, suggesting that the reaction needs a stoichiometric or excess amount of CuBr$_2$. For comparison, conditions under which a similar bromination was known to be catalytic in the literature (Zhang, W. L.; et al. Org. Biomol. Chem. 2015, 13, 3602-3609; Evans, R. W.; et al. J. Am. Chem. Soc. 2013, 135, 16074-16077.) were emulated (Table 1, entry 15 and 16) but these failed to generate any of the desired product. It was speculated that coordination of the bases used (DIPEA and pyridine) to copper led to deactivation of the bromination system. However, the proposed use of 2,6-di-tert-butylpyridine as a non-coordinating base/proton sponge to negate decomposition was also unsuccessful (Table 1, entry 17). It was therefore concluded that the scavenging of protons by the bases was in fact causing deactivation and that the reaction is incompatible with a basic environment. This may be to do with the redox characteristics of the system.

While not intending to be bound by theory, the system described in Scheme 2 is proposed as the principle mechanistic pathway, in which two equivalents of CuBr$_2$ are required. Initially a transient α-bromo intermediate (1e) is formed which undergoes rapid elimination to give DHH (the initial formation of the relevant phenol acetate (Table 2, entry 14b) served as evidence for the formation of acetyl bromide). The evolution of acidic gas was also observed, this was presumably due to HBr which can promote competitive deacetylative decomposition of the starting material 1a, giving the saturated compound 1c. The rate of the oxidation pathway is far quicker than the decomposition which is, in turn, quicker than the re-oxidation of Cu(I) to Cu(II) by the following known equation; $2HBr + \frac{1}{2}O_2 + 2CuBr \rightarrow 2CuBr_2 + H_2O$. Sequestering of the HBr by formation of AcBr would also be destructive with regards to the potential copper re-oxidation sequence.

Scheme 2: Proposed oxidation/decomposition pathway for enol acetate, 1a.

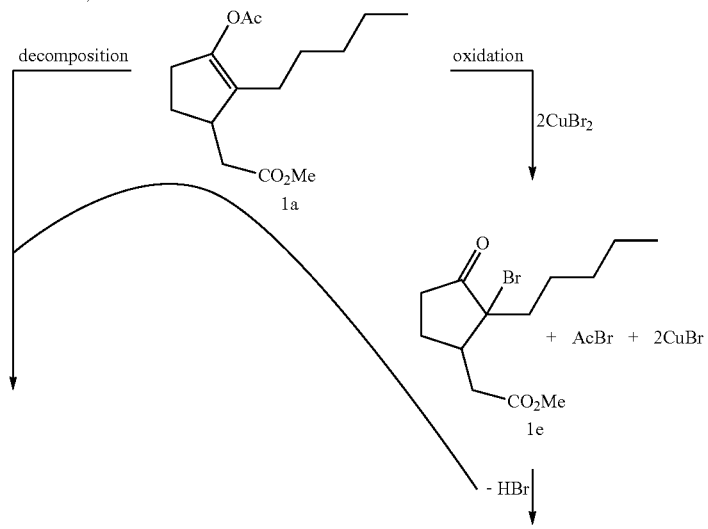

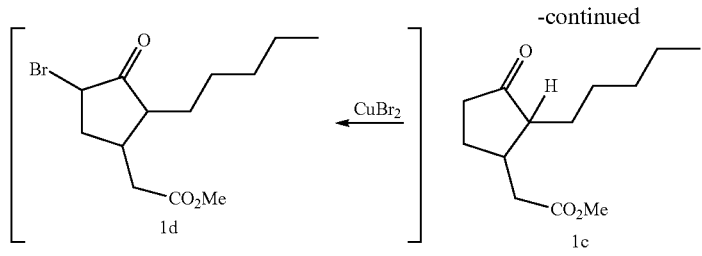
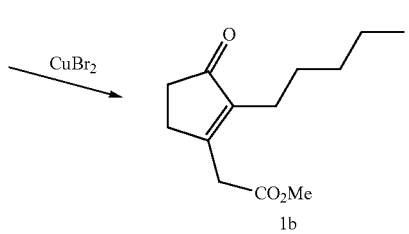

These indications imply that making the system work catalytically would be very difficult based upon the current acyl enol starting material 1a. The potential alternative approach, utilizing the parent ketone directly, which eliminates any potential decomposition, unfortunately creates alternative problems based upon regioselective bromination/oxidation. This was found to be the case upon direct treatment of Hedione® with $CuBr_2$ in MeCN which resulted in a mixture of secondary elimination (1b) and bromination (1d) products (2.1:1 respectively (GC-MS)).

With a viable set of conditions in hand, however, the scope of the transformation was further investigated (Table 2). As indicated above, for unsymmetrical enolisable ketones, double bond regioselectivity could be problematic in the initial enol acetate forming step leading to mixtures of products further down the line. Using Hedione, which exclusively gave a single enol acetate, none of the undesired enol bond isomer was observed. This was only problematic in certain cases (2a-6a, ratios given) as easily identified by the characteristic olefinic signal in the $^1$H-NMR (typically ~5.5 ppm). This is an obvious limitation to the methodology as these, in turn, if not separated, give rise to α-bromo intermediates which lead to different products. A selection of substrates for which this would not be an issue were therefore also investigated (Table 2, entries 7-13).

TABLE 2

Substrate scope investigation.

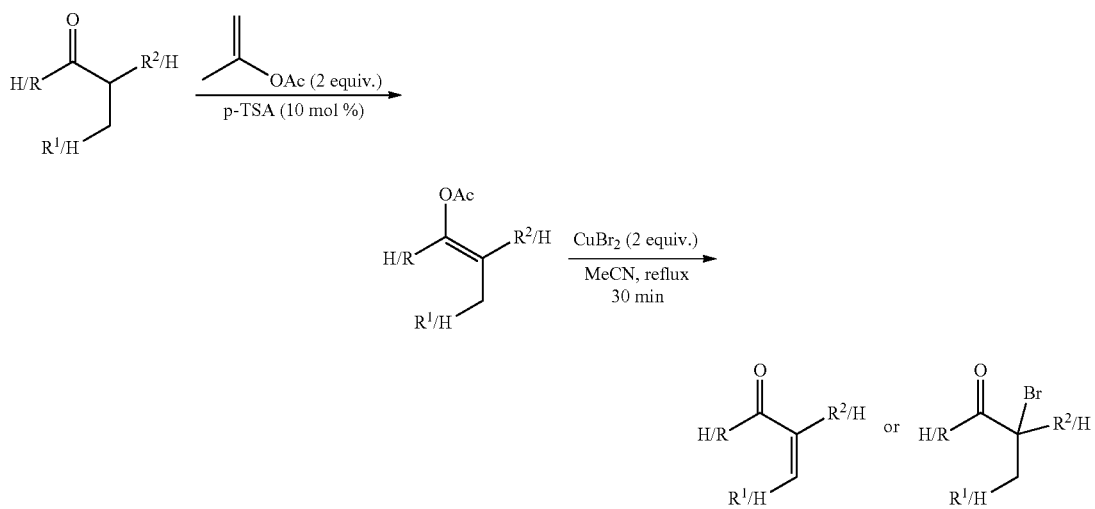

| Entry | Starting material | Yield (%)[a] | Entry | Product | Yield (%)[a] |
|---|---|---|---|---|---|
| 1a | | 97[b] | 1b | | 99[b] |
| 2a | | 64 (3:1) | 2b | | 90[c] |

TABLE 2-continued
Substrate scope investigation.
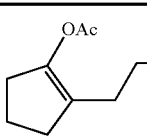
| Entry | Starting material | Yield (%)[a] | Entry | Product | Yield (%)[a] |
|---|---|---|---|---|---|
| 3a | 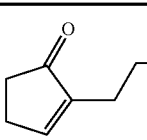 | 70 (8:1) | 3b | 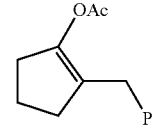 | 89[c] |
| 4a | 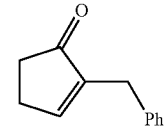 [SMILES: O=C1CCC=C1Cc1ccccc1] | 78 (2:1) | 4b | 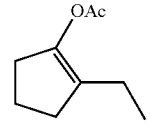 | 20[c] |
| 5a | 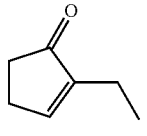 | 75 (1:1) | 5b | 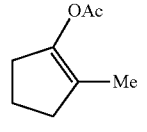 | 62[c] |
| 6a | 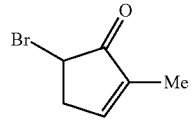 | 53 (6:1) | 6b | 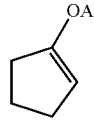 | 17 |
| 7a | 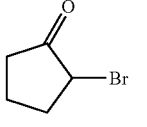 | 76 | 7b | 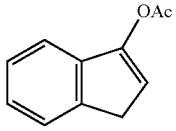 | 31 |
| 8a | 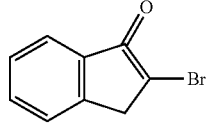 | 73 | 8b | 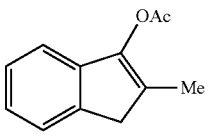 [SMILES: CC(=O)OC1=C(C)Cc2ccccc21] | 83 |
| 9a | 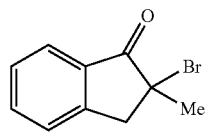 | 55 | 9b |  | 68 |

TABLE 2-continued

Substrate scope investigation.

| Entry | Starting material | Yield (%)[a] | Entry | Product | Yield (%)[a] |
|---|---|---|---|---|---|
| 10a | (cyclopentene with OAc and CO₂Me) | 74 | 10b | — | N/A |
| 11a | (dienol acetate) | 67 | 11b | (α-bromo ketone with isoprenyl) | 46 |
| 12a | (cyclohexylidene methyl acetate) | 64[d] | 12b | (1-bromocyclohexanecarbaldehyde) | 86 |
| 13a | (α-methylstyrene enol acetate) | 89 | 13b | (Me, OH, phenyl aldehyde) | 57 |
| 14a | (cyclohexenyl acetate with pentyl) | 57 | 14b | (2-pentylphenol) | 42 |

Notes:
[a]Isolated yields after SiO₂ column chromatography.
[b]Chromatography not necessary.
[c]Yields reported relative to correct enol acetate isomer.
[d]MsOH (10 mol %) and 4 equivalents isopropenyl acetate was used.

Starting material consumption was quantitative in all cases (as determined by TLC). A general trend was observed regarding spontaneous elimination of the initially formed bromo intermediate. For the 2-substituted cyclopentanone derivatives, the pendant alkyl chain induced elimination at lengths down to the ethyl, where incomplete elimination was observed. For both α-methyl cyclopentanone (6b) and α-methyl indanone (9b) mixtures of α-bromo and α,β-unsaturated products were observed. In the case of 6a, a complex mixture of products was obtained with 6b being the only isolable product after flash column chromatography. The unfunctionalised derivatives, 7a and 8a, yielded exclusively α-bromo adducts (7b and 8b respectively). This trend suggests that steric impingement at the α-position is key in determining whether the substrate undergoes full elimination under the reaction conditions. Interestingly, the oxidation of 4a led exclusively to the formation of the endocyclic, less conjugated double bond isomer. Of the linear carbonyls tested, only α-bromination was observed. For the phenyl-propenyl acetate, 13a, the α-bromo adduct formed initially, but underwent rapid hydrolysis during purification.

Interestingly, the cyclohexanone derivative, 14a, underwent successive oxidation furnishing the corresponding phenol (14b). The formation of phenols from α,β-unsaturated cyclohexanone starting materials using copper(II) salts is a known process and was first reported over 50 years ago (Kochi, J. K. *J. Am. Chem. Soc.* 1955, 77, 5274-5278.). However, taking an enol-cyclohexanone through a single-step, two-level oxidation process, to our knowledge, has never been performed. While not intending to be bound by theory, a plausible mechanistic rationalization is depicted in Scheme 3 below. Thus, another aspect of the present invention includes synthesis of phenol derivatives by $CuBr_2$-mediated oxidation of enol acetate intermediates of the corresponding cyclohexane derivatives.

Based upon the information acquired from the above studies, the potential for a catalytic system was again considered (in which a ketone would be treated with substoichiometric $CuBr_2$). In this system, bromination should be biased to only occur on one side of the ketone, leading to an elimination product which could not be brominated a second time. It was hoped that this would allow for complete conversion of the ketone by using substoichiometric quantities of $CuBr_2$ as a basic proof of principle.

Scheme 3: Proposed phenol formation mechanisitc routes.

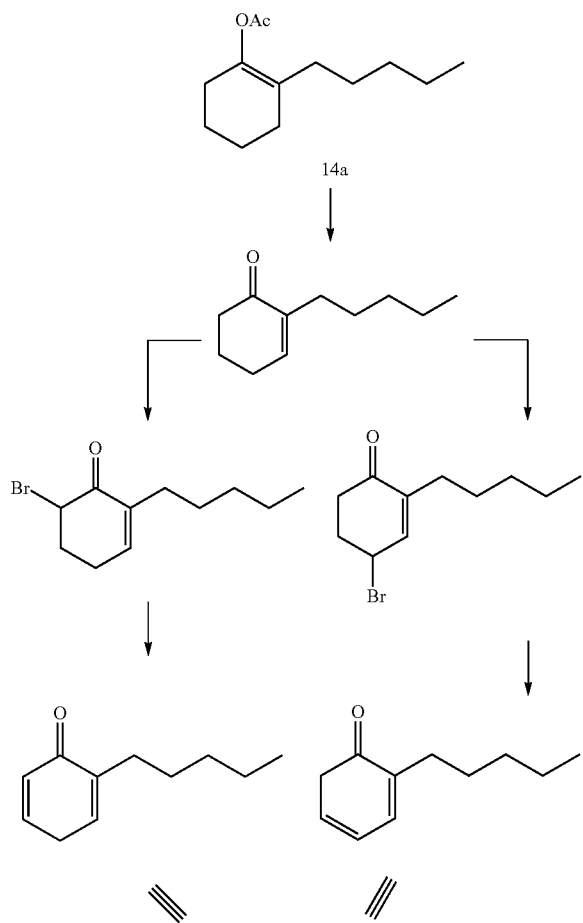

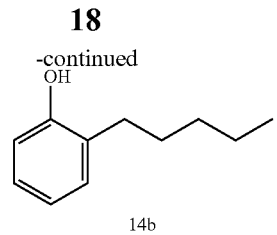

14b

Scheme 4: Substrates employed for catalytic system.

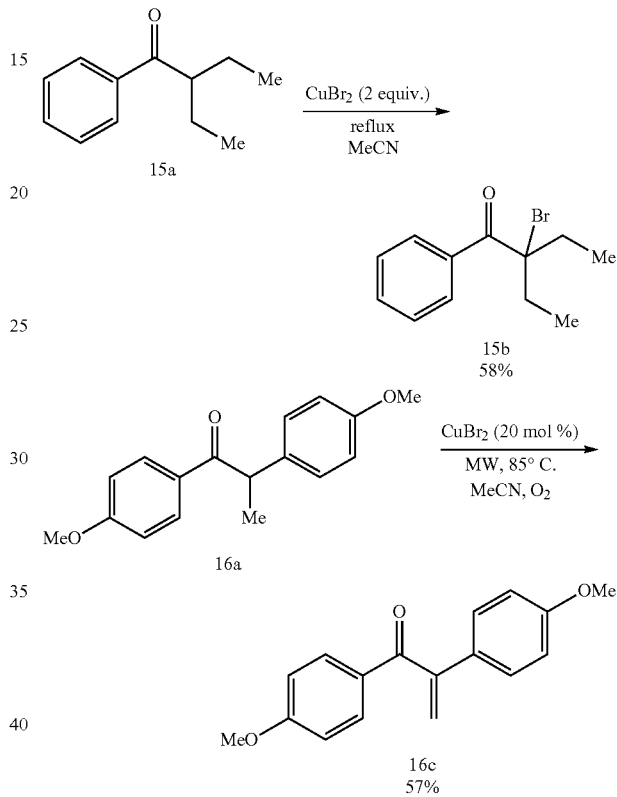

The first of these (15a) was unsuccessful due to the formation of exclusively the α-bromo adduct, 15b. No subsequent elimination was observed; even upon treatment with 2 equivalents of $CuBr_2$, only product 15b was isolated (58% yield). A second substrate, a desoxyansoin derivative, 16a, was treated with 20 mol % of $CuBr_2$ and subjected to microwave heating (85° C.). The reaction progress was monitored by GC-MS analysis and the solvent was purged with further $O_2$ between each sampling period. After 132 h, >85% conversion of the starting material (16a) was estimated and the reaction was worked-up. After purification by column chromatography and removal of a decomposition product (17) under high vacuum, 16c was obtained in 57% isolated yield. To be sure that the oxidation was not proceeding via an alternative route, for example, an α-hydroxylation, the reaction was repeated in an $O_2$ atmosphere with $Cu(OAc)_2$ and without any catalyst. Neither of these resulted in any conversion of the starting material. The α-bromo adduct (16b), was observed in the crude reaction mixture by ASAP-MS (accurate mass obtained, Δ=0.9 ppm) supporting the proposed catalytic cycle (Scheme 5).

While not intending to be bound, the mechanism of $CuBr_2$ catalyzed oxidation of compound 16a is believed to be through the proposed cycle in Scheme 5, in which the elimination step leads to the formation of HBr, allowing for the reoxidation of Cu(I) in the presence of oxygen to regenerate the brominating agent, CuBr$_2$. Decomposition of the product to 4-acetylanisole (17) was also observed under the acidic reaction conditions; this was presumably aided by the electron donating para-methoxy group on the aromatic rings. A possible mechanism for the formation of compound 17 is given in Scheme 5.

Scheme 5: Proposed catalytic cycle for the oxidation of 16a.

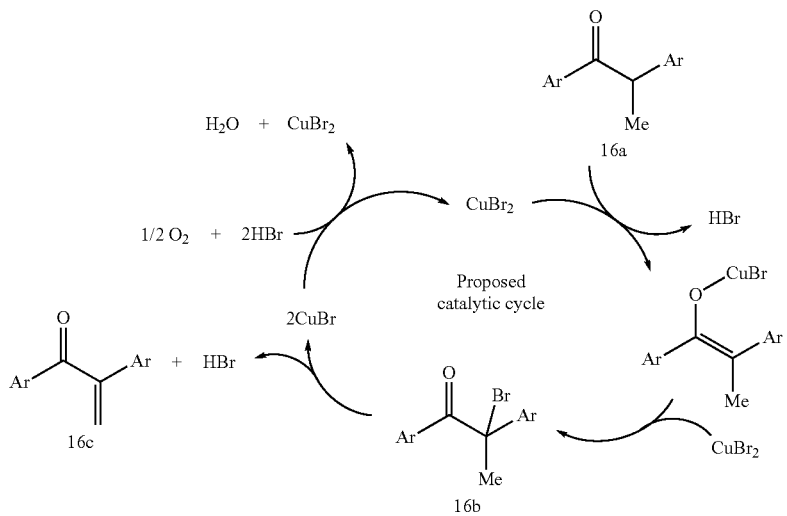

Scheme 6: Possible mechanistic pathway for the acid catalysed decomposition of 16c.

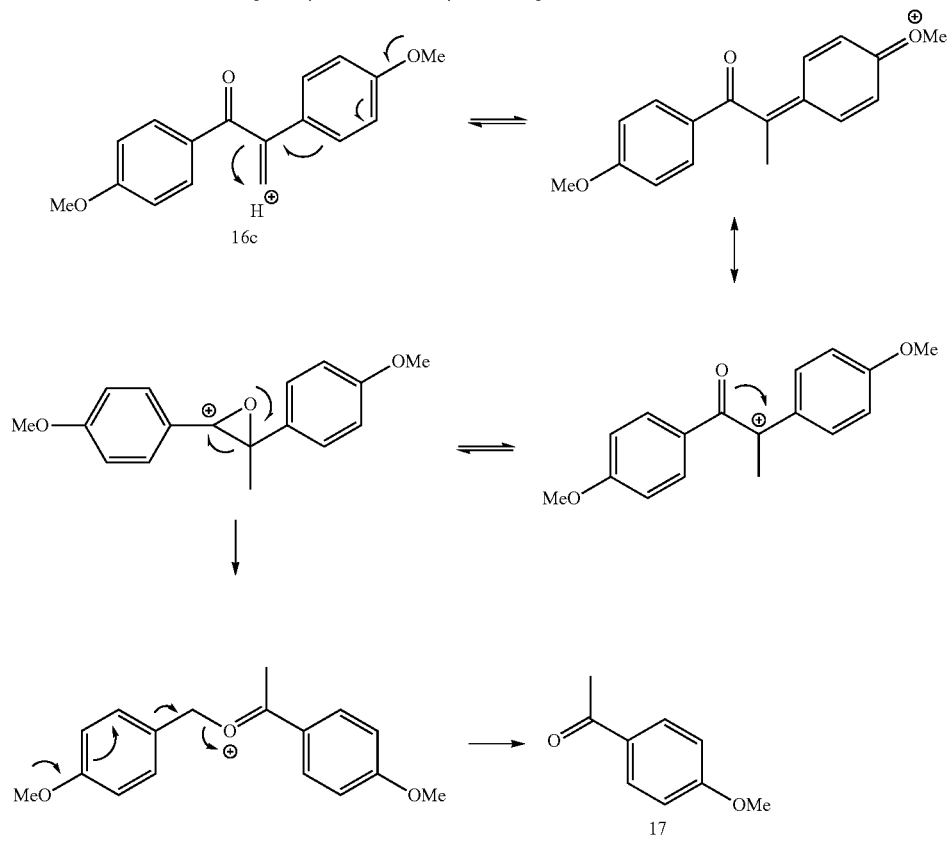

The cycle described highlights the key attributes of the process and acts as a proof of concept, revealing that CuBr$_2$ can be used as a catalytic oxidant to convert certain ketones to their corresponding α,β-unsaturated analogues. Further work is underway to gain more insight into the potential of this process for use in industrial oxidation processes.

In conclusion, the methodology developed proved highly effective for the two-step synthesis of DHH from Hedione® and its applicability to other substrates was demonstrated and explored. We have shown that in-situ elimination is specific to substrates bearing sufficiently bulky functional groups at the α-position. In addition, a catalytic system was developed which served as a mechanistic probe to gain better insight into the process. Efforts directed towards further development of the catalytic system are currently underway and work towards a system in which phenols can be formed from cyclohexanones, catalytically is also ongoing.

EXAMPLES

General Method

Unless otherwise stated, all solvents were purchased from Fisher Scientific and used without further purification. Substrates and their precursors and reagents were purchased from Alfa Aesar or Sigma Aldrich and used as received.

$^1$H-NMR spectra were recorded on either Bruker Avance-400 or Varian VNMRS-700 instruments and are reported relative to residual solvent: CHCl$_3$ (δ 7.26 ppm). $^{13}$C-NMR spectra were recorded on the same instruments and are reported relative to CHCl$_3$ (δ 77.16 ppm). Data for $^1$H-NMR are reported as follows: chemical shift (δ/ppm) (multiplicity, coupling constant (Hz), integration). Multiplicities are reported as follows: s=singlet, d=doublet, t=triplet, q=quartet, p=pentet, m=multiplet, br. s=broad singlet, app.=apparent. Data for $^{13}$C-NMR are reported in terms of chemical shift (δ$_C$/ppm). DEPT-135, COSY, HSQC, HMBC and NOESY experiments were used in structural assignments. The $^1$H and $^{13}$C-NMR spectra of selected examples prepared are provided for illustration in the present application.

IR spectra were obtained using a Perkin Elmer Spectrum Two UATR Two FT-IR Spectrometer (neat, ATR sampling) with the intensities of the characteristic signals being reported as weak (w, <20% of tallest signal), medium (m, 21-70% of tallest signal) or strong (s, >71% of tallest signal). Low and high resolution mass spectrometry was performed using the indicated techniques. Gas chromatography mass spectrometry (GC-MS) was performed on a Shimadzu QP2010-Ultra equipped with an Rxi-55Sil MS column in EI mode. Atmospheric solids analysis probe mass spectrometry (ASAP-MS) was performed using a Waters LCT Premier XE. For accurate mass measurements the deviation from the calculated formula is reported in ppm. Melting points were recorded on an Optimelt automated melting point system with a heating rate of 1° C./min and are uncorrected.

General Procedure for Acetylation of Ketones/Aldehydes

For a typical 10 mmol scale reaction, the starting material was dissolved in isopropenyl acetate (2.2 mL, 2 equivalents) and para-toluene sulfonic acid (0.2 g, 10 mol %) was added. The resulting mixture was stirred at 90° C. until full conversion was achieved (TLC). Saturated aqueous NaHCO$_3$ (15 mL) and Et$_2$O (20 mL) were added and the products were extracted using further Et$_2$O (2×20 mL). After drying over Na$_2$SO$_4$ and concentration in vacuo, crude products were purified using SiO$_2$ column chromatography (hexane/EtOAc) where necessary.

Example 1. Methyl 2-(3-acetoxy-2-pentylcyclopent-2-en-1-yl)acetate (1a)

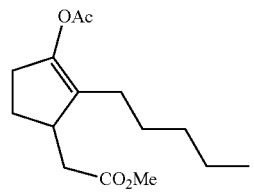

Chemical Formula: C$_{15}$H$_{24}$O$_4$

Pale brown liquid (5 mmol scale, 1.31 g, 98%). $^1$H NMR (400 MHz, CDCl$_3$) δ 3.70 (s, 3H), 3.07 (m, 1H), 2.56 (dd, J=4.4, 14.8 Hz, 1H), 2.48 (m, 2H), 2.14 (s, 3H), 2.07-2.24 (m, 3H), 1.80 (m, 1H), 1.63 (m, 1H), 1.42 (m, 1H), 1.27 (m, 5H), 0.90 (t, J=7.9 Hz, 3H) ppm; $^{13}$C NMR (100 MHz, CDCl$_3$) δ$_C$ 173.3, 168.6, 145.2, 128.3, 51.5, 39.5, 38.6, 31.7, 29.6, 27.1, 26.7, 24.4, 22.4, 20.8, 14.0 ppm; FT-IR ν$_{max}$ 1008 (m), 1204 (s), 1368 (m), 1436 (w), 1737 (s), 2930 (w) cm$^{-1}$; GC-MS R$_t$ 4.79 min, m/z 268 [M]$^+$, 226 [M-Ac]$^+$.

Example 2. 3-Methyl-2-pentylcyclopent-1-en-1-yl acetate (2a)

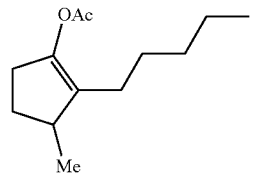

Chemical Formula: C$_{13}$H$_{22}$O$_2$

Starting material obtained by organocuprate conjugate addition of 2-pentyl cyclopent-2-enone (Ravid, U. and Ikan, R. *J. Org. Chem.* 1974, 78, 2637-2639). Pale yellow liquid (2 mmol scale, 375 mg, 86%), (3:1 isomer ratio). $^1$H NMR (400 MHz, CDCl$_3$) δ 2.70 (m, 1H), 2.45 (m, 2H), 2.16 (s, 3H), 2.15-1.81 (m, 2H), 1.51-1.22 (m, 8H), 1.05 (d, J=6.9 Hz, 3H), 0.90 (t, J=7.0 Hz, 3H) ppm; $^{13}$C NMR (100 MHz, CDCl$_3$) δ$_C$ 168.8, 143.8, 130.8, 37.3, 31.7, 29.7, 29.4, 26.7, 24.4, 22.4, 20.8, 19.6, 14.0 ppm; FT-IR ν$_{max}$ 1202 (s), 1180 (s), 1369 (w), 1756 (m), 2859 (w), 2929 (w), 2956 (w) cm$^{-1}$; GC-MS R$_t$ 3.85 min, m/z 210 [M]$^+$, 168 [M-Ac]$^+$.

Example 3. 2-Pentylcyclopent-1-en-1-yl acetate (3a)

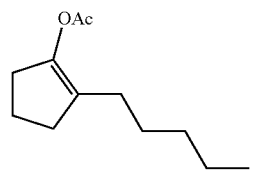

Chemical Formula: C$_{12}$H$_{20}$O$_2$

Starting material obtained by hydrogenation of 2-pentyl cyclopent-2-enone (aldol product of cyclopentanone and pentanal). Colourless liquid (2.5 mmol scale, 295 mg, 70%), (8:1 isomer ratio). 1H NMR (400 MHz, CDCl$_3$) δ 2.48 (m, 2H), 2.31 (m, 2H), 2.17 (s, 3H), 2.03-1.88 (m, 4H), 1.42-1.21 (m, 6H), 0.90 (t, J=7.1 Hz, 3H) ppm. 13C NMR (100 MHz, CDCl$_3$) δ$_C$ 168.9, 143.8, 126.9, 31.6, 31.1, 31.0, 26.8, 26.4, 22.5, 20.8, 19.8, 14.0 ppm; FT-IR ν$_{max}$ 1210 (s), 1739 (s), 2859 (w), 2930 (m), 2956 (m) cm$^{-1}$; GC-MS R$_t$ 3.76 min, m/z 196 [M]$^+$, 154 [M-Ac]$^+$.

Example 4. 2-Benzylcyclopent-1-en-1-yl acetate (4a)

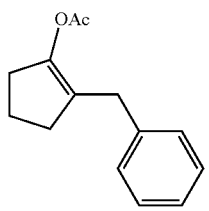

Chemical Formula: C$_{14}$H$_{16}$O$_2$

Starting material obtained from 2-cyclopentylidene-1,1-dimethylhydrazine (Mino, T.; et al. *J. Org. Chem.* 1997, 62, 2633-2635). Colourless liquid (3.5 mmol scale, 592 mg, 78%), (2:1 isomer ratio). $^1$H NMR (400 MHz, CDCl$_3$) δ 7.34-7.16 (m, 5H), 3.34 (s, 2H), 2.51-2.58 (m, 2H), 2.26-2.19 (m, 2H), 2.17 (s, 3H), 1.97-1.87 (m, 2H) ppm; $^{13}$C NMR (100 MHz, CDCl$_3$) δ$_C$ 169.0, 144.9, 139.0, 128.7, 128.3, 126.0, 125.9, 33.0, 31.1, 31.0, 20.8, 19.7 ppm; FT-IR ν$_{max}$ 699 (m), 753 (m), 1205 (s), 1366 (s), 1746 (s), 2970 (m) cm$^{-1}$; GC-MS R$_t$ 4.80 (major)+4.86 min, m/z 216 [M]$^+$, 174 [M-Ac]$^+$.

Example 5. 2-Ethylcyclopent-1-en-1-yl acetate (5a)

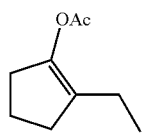

Chemical Formula: C$_9$H$_{14}$O$_2$

Starting material obtained from 2-cyclopentylidene-1,1-dimethylhydrazine (Mino, T.; et al. *J. Org. Chem.* 1997, 62, 2633-2635). Colourless oil (1 mmol scale, 115 mg, 75%), (1:1 isomer ratio). $^1$H NMR (700 MHz, CDCl$_3$) δ 2.47-2.42 (m, 2H), 2.32-2.28 (m, 2H), 2.13 (s, 3H), 2.01-1.96 (m, 2H), 1.89 (m, 2H), 0.95 (t, J=7.6 Hz, 3H) ppm; $^{13}$C NMR (176 MHz, CDCl$_3$) δ$_C$ 168.9, 143.0, 128.1, 31.0, 30.7, 21.1, 19.7, 19.6, 11.9 ppm; FT-IR ν$_{max}$ 1178 (s), 1199 (s), 1369 (m), 1751 (m), 2971 (m) cm$^{-1}$; GC-MS R$_t$ 2.99 min, m/z 154 [M]$^+$, 112 [M-Ac]$^+$.

Example 6. 2-Methylcyclopent-1-en-1-yl acetate (6a)

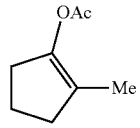

Chemical Formula: C$_8$H$_{12}$O$_2$

Starting material obtained from 2-cyclopentylidene-1,1-dimethylhydrazine (Mino, T.; et al. *J. Org. Chem.* 1997, 62, 2633-2635). Colourless liquid (1 mmol scale, 74 mg, 53%), (6:1 isomer ratio). $^1$H NMR (400 MHz, CDCl$_3$) δ 2.47 (m, 2H), 2.31 (m, 2H), 2.17 (s, 3H), 1.97-1.88 (m, 2H), 1.56 (m, 3H) ppm; $^{13}$C NMR (100 MHz, CDCl$_3$) δ$_C$ 168.9, 143.9, 122.7, 33.5, 30.9, 20.8, 19.7, 11.9 ppm; FT-IR ν$_{max}$ 1073 (w), 1180 (s), 1208 (s), 1369 (w), 1751 (m), 2925 (w) cm$^{-1}$; GC-MS R$_t$ 2.70 min, m/z 140 [M]$^+$, 98 [M-Ac]$^+$.

Example 7. Cyclopent-1-en-1-yl acetate (7a)

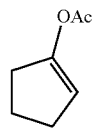

Chemical Formula: C$_7$H$_{10}$O$_2$

Pale brown liquid (20 mmol scale, 1.90 g, 76%). $^1$H NMR (400 MHz, CDCl$_3$) δ 5.41 (m, 1H), 2.46 (m, 2H), 2.38 (m, 2H), 2.16 (s, 3H), 1.95 (m, 2H) ppm; 13C NMR (100 MHz, CDCl$_3$) 6c 168.7, 150.9, 113.1, 30.9, 28.6, 21.1, 21.0 ppm; FT-IR ν$_{max}$ 1153 (w), 1201 (s), 1341 (w), 1370 (w), 1666 (w), 1755 (s), 2856 (w), 2928 (m) cm$^{-1}$; GC-MS R$_t$ 3.62 min, m/z 126 [M]$^+$, 84 [M-Ac]$^+$.

Example 8. 1H-Inden-3-yl acetate (8a)

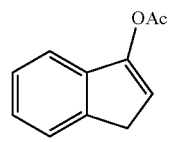

Chemical Formula: C$_{11}$H$_{10}$O$_2$

White crystalline solid, m.p. 48-49° C. (petroleum ether), (lit. 48.5-49.5° C.), (1.4 mmol scale, 182 mg, 73%). $^1$H NMR (400 MHz, CDCl$_3$) δ 7.47 (d, J=7.3 Hz, 1H), 7.36-7.25 (m, 3H), 6.36 (t, J=2.3 Hz, 1H), 3.45 (d, J=2.4 Hz, 2H), 2.37 (s, 3H) ppm; $^{13}$C NMR (100 MHz, CDCl$_3$) δ$_C$ 168.3, 149.1, 141.8, 139.0, 126.3, 125.7, 124.1, 118.0, 115.6, 35.0, 21.2 ppm; FT-IR ν$_{max}$ 1007 (m), 1074 (m), 1112 (m), 1166 (m), 1207 (s), 1361 (m), 1725 (s) cm$^1$; GC-MS R$_t$ 4.07 min, m/z 174 [M]$^+$, 132 [M-Ac]$^+$.

Example 9. 2-Methyl-1H-inden-3-yl acetate (9a)

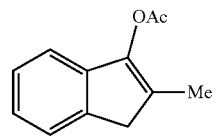

Chemical Formula: $C_{12}H_{12}O_2$

Starting material obtained from 2-(2,3-dihydro-1H-inden-1-ylidene)-1,1-dimethylhydrazine. [27]Yellow oil (5 mmol scale, 515 mg, 55%). $^1$H NMR (400 MHz, CDCl$_3$) δ 7.37 (d, J=7.6 Hz, 1H), 7.27 (m, 1H), 7.17 (td, J=7.4, 1.2 Hz, 1H), 7.09 (d, J=7.6 Hz, 1H), 3.36 (s, 2H), 2.39 (s, 3H), 2.01 (s, 3H) ppm; $^{13}$C NMR (100 MHz, CDCl$_3$) δ$_C$ 168.4, 144.4, 140.2, 139.8, 128.4, 126.2, 124.6, 123.7, 117.1, 39.1, 20.6, 12.3 ppm; FT-IR ν$_{max}$ 715 (m), 749 (s), 1122 (m), 1197 (s), 1365 (m), 1752 (s) cm$^{-1}$; GC-MS R$_t$ 4.07 min, m/z 188 [M]$^+$, 146 [M-Ac]$^+$.

Example 10. Methyl 2-acetoxycyclopent-1-enecarboxylate (10a)

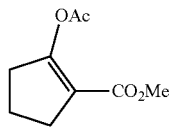

Chemical Formula: $C_9H_{12}O_4$

Colourless liquid (5 mmol scale, 680 mg, 74%). $^1$H NMR (400 MHz, CDCl$_3$) δ 3.73 (s, 3H), 2.70-2.61 (m, 4H), 2.25 (s, 3H), 2.01-1.94 (m, 2H) ppm; $^{13}$C NMR (100 MHz, CDCl$_3$) δ$_C$ 167.7, 164.1, 160.0, 118.0, 51.3, 33.5, 29.4, 20.9, 19.1 ppm; FT-IR ν$_{max}$ 1043 (m), 1132 (m), 1174 (s), 1217 (s), 1366 (s), 1717 (s), 1739 (s), 2971 (m) cm$^{-1}$; GC-MS R$_t$ 3.65 min, m/z 184 [M]$^+$, 142 [M-Ac]$^+$.

Example 11. 6-Methylhepta-2,5-dien-2-yl acetate (11a)

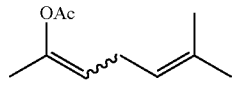

Chemical Formula: $C_{10}H_{16}O_2$

Pale yellow liquid (20 mmol scale, 2.25 g, 67%), (~1:1 mixture of E/Z isomers). $^1$H NMR (400 MHz, CDCl$_3$) δ 4.75-5.14 (m, 2H), 2.20-2.74 (m, 2H), 2.18 (s, 1.5H), 2.16 (s, 1.5H), 1.89 (m, 3H), 1.70 (m, 3H), 1.63 (m, 3H) ppm; $^{13}$C NMR (100 MHz, CDCl$_3$) δ$_C$ 169.2, 168.9, 156.2, 144.6, 132.5, 122.9, 121.5, 115.8, 101.3, 33.4, 25.7, 25.6, 25.1, 24.5, 21.1, 20.8, 19.5, 17.7, 17.6, 15.2 ppm; FT-IR ν$_{max}$ 1217 (s), 1370 (s), 1752 (s), 2971 (m) cm$^{-1}$; GC-MS R$_t$ 3.16+3.29 min, m/z 168 [M]$^+$, 126 [M-Ac]$^+$.

Example 12. Cyclohexylidenemethyl acetate (12a)

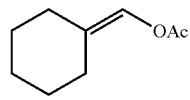 [SMILES: CC(=O)OC=C1CCCCC1]

Chemical Formula: $C_9H_{14}O_2$

Methanesulfonic acid (10 mol %) and 4 equivalents of isopropenyl acetate used. Pale yellow liquid (10 mmol scale, 980 mg, 64%). $^1$H NMR (400 MHz, CDCl$_3$) δ 6.87 (t, J=1.2 Hz, 1H), 2.25 (m, 2H), 2.15 (s, 3H), 2.06 (m, 2H), 1.61-1.48 (m, 6H). $^{13}$C NMR (100 MHz, CDCl$_3$) δ$_C$ 168.6, 127.1, 125.7, 30.6, 27.9, 26.8, 26.5, 26.2, 20.8; FT-IR ν$_{max}$ 1204 (s), 1220 (s), 1745 (s), 2854 (w), 2927 (m) cm$^{-1}$; GC-MS R$_t$ 3.27 min, m/z 154 [M]$^+$, 112 [M-Ac]$^+$.

Example 13. 2-Phenylprop-1-en-1-yl acetate (13a)

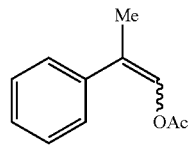

Chemical Formula: $C_{11}H_{12}O_2$

Yellow liquid (10 mmol scale, 1.56 g, 89%), (3.3:1 mixture of E:Z isomers). $^1$H NMR (400 MHz, CDCl$_3$) δ 7.57-7.22 (m, 6H), 2.25 (s, 3H, (E)), 2.15 (s, 3H, (Z)), 2.12 (d, J=1.5 Hz, 3H, (E)), 2.05 (d, J=1.5 Hz, 3H, (Z)) ppm; $^{13}$C NMR (100 MHz, CDCl$_3$) δ$_C$ E: 168.0, 139.1, 132.6, 128.5, 127.3, 125.8, 121.6, 20.9, 13.6 ppm; FT-IR ν$_{max}$ 1067 (m), 1117 (s), 1209 (s), 1369 (m), 1752 (s) cm$^{-1}$; GC-MS R$_t$ 3.74+3.91 (major) min, m/z 176 [M]$^+$, 134 [M-Ac]$^+$.

Example 14. 2-Pentylcyclohex-1-en-1-yl acetate (14a)

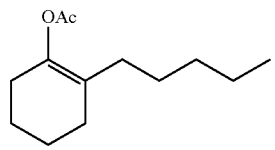

Chemical Formula: $C_{13}H_{22}O_2$

Starting material obtained by hydrogenation of 2-pentylidenecyclohexanone (aldol product of cyclohexanone and pentanal). Colourless liquid (1.1 mmol scale, 135 mg, 57%). $^1$H NMR (400 MHz, CDCl$_3$) δ 2.15 (s, 3H), 2.15-2.06 (m, 4H), 1.92 (t, J=7.7 Hz, 2H), 1.73-1.62 (m, 4H), 1.40-1.21 (m, 6H), 0.90 (t, J=7.1 Hz, 3H) ppm; $^{13}$C NMR (100 MHz, CDCl$_3$) δ$_C$ 169.4, 141.9, 124.5, 31.7, 30.1, 27.7, 27.1, 26.9, 23.1, 22.5, 22.5, 20.9, 14.0 ppm; FT-IR ν$_{max}$ 730 (m), 907 (m), 1111 (m), 1217 (s), 1369 (m), 1750 (s), 2930 (m) cm$^{-1}$; GC-MS R$_t$ 4.03 min, m/z 210 [M]$^+$, 168 [M-Ac]$^+$.

General Procedure for the Oxidation/Bromination of Enol Acetates

For a typical 1 mmol scale reaction, the enol acetate was dissolved in MeCN (5 mL).

Copper(II) bromide (0.45 g, 2 equivalents) was then added and the mixture was stirred under reflux until full conversion was observed (TLC). The resultant mixture was allowed to cool and after removal of MeCN in vacuo, was partitioned between $H_2O$ (10 mL) and $Et_2O$ (15 mL). Products were extracted using further $Et_2O$ (2×15 mL). After drying over $Na_2SO_4$ and concentration in vacuo, crude products were purified using $SiO_2$ column chromatography (hexane/EtOAc) where necessary.

Example 15. Methyl 2-(3-oxo-2-pentylcyclopent-1-en-1-yl)acetate (1b)

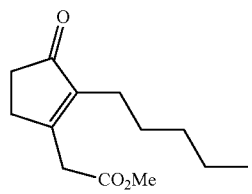

Chemical Formula: $C_{11}H_{18}O$

Colourless liquid (1 mmol scale, 220 mg, 99%). $^1$H NMR (400 MHz, CDCl$_3$) δ 3.74 (s, 3H), 3.46 (s, 2H), 2.63 (m, 2H), 2.42 (m, 2H), 2.19 (m, 2H), 1.21-1.44 (m, 6H), 0.88 (t, J=8.0 Hz, 3H) ppm; $^{13}$C NMR (100 MHz, CDCl$_3$) δ$_C$ 209.2, 169.6, 163.3, 143.3, 52.3, 36.6, 34.3, 31.8, 29.7, 28.0, 23.2, 22.5, 14.0 ppm; FT-IR ν$_{max}$ 1171 (s), 1194 (s), 1435 (m), 1644 (m), 1698 (s), 1738 (s), 2860 (w), 2929 (w), 2954 (w) cm$^{-1}$; GC-MS R$_t$ 4.70 min, m/z 224 [M]$^+$, 193 [M-OMe]$^+$, 154 [M-C$_5$H$_{11}$]$^+$, 151 [M-CH$_2$CO$_2$Me]$^+$.

Example 16. 3-Methyl-2-pentylcyclopent-2-enone (2b)

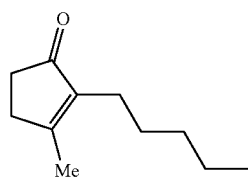

Chemical Formula: $C_{11}H_{18}O$

Colourless liquid (1 mmol scale, 75% isomerically pure starting material, 112 mg, 90%). $^1$H NMR (400 MHz, CDCl$_3$) δ 2.50 (m, 2H), 2.37 (m, 2H), 2.17 (t, J=7.6 Hz, 2H), 2.06 (s, 3H), 1.43-1.21 (m, 6H), 0.88 (t, J=7.2 Hz, 3H) ppm; $^{13}$C NMR (100 MHz, CDCl$_3$) δ$_C$ 209.7, 170.0, 140.8, 34.3, 31.8, 31.5, 28.1, 23.0, 22.5, 17.2, 14.0 ppm; FT-IR ν$_{max}$ 1385 (w), 1645 (m), 1695 (s), 2858 (w), 2926 (w), 1956 (w) cm$^{-1}$; GC-MS R$_t$ 3.89 min, m/z 166 [M]$^+$, 151 [M-Me]$^+$.

Example 17. 2-Pentylcyclopent-2-enone (3b)

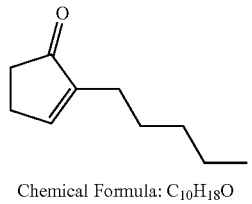

Chemical Formula: $C_{10}H_{18}O$

Pale yellow liquid (1 mmol scale, 90% isomerically pure starting material, 122 mg, 89%). $^1$H NMR (400 MHz, CDCl$_3$) δ 7.31 (m, 1H), 2.60-2.54 (m, 2H), 2.43-2.38 (m, 2H), 2.17 (m, 2H), 1.54-1.44 (m, 2H), 1.38-1.24 (m, 4H), 0.90 (t, J=6.8 Hz, 3H) ppm; $^{13}$C NMR (100 MHz, CDCl$_3$) δ$_C$ 210.1, 157.2, 146.6, 34.6, 31.6, 27.4, 26.4, 24.7, 22.4, 14.0 ppm; FT-IR ν$_{max}$ 1696 (s), 2860 (w), 2926 (w), 2956 (w) cm$^{-1}$; GC-MS R$_t$ 3.63 min, m/z 152 [M]$^+$, 137 [M-Me]$^+$, 123 [M-Et]$^+$.

Example 18. 2-Benzylcyclopent-2-enone (4b)

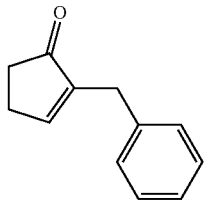

Chemical Formula: $C_{12}H_{12}O$

Colourless liquid (1 mmol scale, 67% isomerically pure starting material, 22 mg, 20%). $^1$H NMR (400 MHz, CDCl$_3$) δ 7.35-7.20 (m, 5H), 7.17 (m, 1H), 3.51 (m, 2H), 2.56 (m, 2H), 2.50-2.42 (m, 2H) ppm; $^{13}$C NMR (100 MHz, CDCl$_3$) δ$_C$ 209.2, 158.8, 146.1, 138.9, 128.9, 128.5, 126.3, 34.6, 31.4, 26.5 ppm; FT-IR ν$_{max}$ 703 (m), 790 (w), 1001 (w), 1453 (w), 1496 (w), 1695 (s) cm$^1$; GC-MS R$_t$ 4.37 min, m/z 172 [M]$^+$.

Example 19. 2-Ethylcyclopent-2-enone (5b)

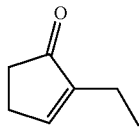

Chemical Formula: $C_7H_{10}O$

Yellow liquid (1 mmol scale, 50% isomerically pure starting material, 31 mg, 62%). $^1$H NMR (400 MHz, CDCl$_3$) δ 7.32 (m, 1H), 2.61-2.55 (m, 2H), 2.45-2.40 (m, 2H), 2.26-2.17 (m, 2H), 1.12 (t, J=7.5 Hz, 3H) ppm; $^{13}$C NMR (100 MHz, CDCl$_3$) δ$_C$ 210.0, 156.6, 147.9, 34.7, 26.4, 18.1, 12.1 ppm; FT-IR ν$_{max}$ 1262 (w), 1715 (s), 2926 (m) cm$^{-1}$; GC-MS R$_t$ 2.67 min, m/z 110 [M]$^+$, 95 [M-Me]$^+$.

Example 20. 5-Bromo-2-methylcyclopent-2-enone (6b)

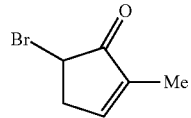

Chemical Formula: C₆H₇BrO

Colourless liquid (1.4 mmol scale, 85% isomerically pure starting material, 35 mg, 17%). $^1$H NMR (400 MHz, CDCl$_3$) δ 7.33 (m, 1H), 5.11 (m, 1H), 3.07 (dd, J=19.6, 6.2 Hz, 1H), 2.79 (dd, J=19.6, 1.6 Hz, 1H), 1.88 (t, J=1.6 Hz, 3H) ppm; $^{13}$C NMR (100 MHz, CDCl$_3$) $δ_C$ 204.7, 156.2, 143.8, 45.2, 42.1, 10.0 ppm; FT-IR $ν_{max}$ 918 (m), 1069 (w), 1187 (w), 1709 (s) cm$^{-1}$; GC-MS R$_t$ 3.13 min, m/z 176 [M]$^+$, 174 [M]$^+$, 95 [M-Br]$^+$; ASAP-HRMS m/z found [M+H]$^+$ 176.9738, C₆H₈BrO requires 176.9738 (Δ=0 ppm).

Example 21. 2-Bromocyclopentanone (7b)

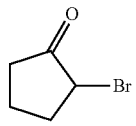

Chemical Formula: C₅H₇BrO

Colourless liquid (1 mmol scale, 51 mg, 31%). $^1$H NMR (400 MHz, CDCl$_3$) δ 4.28-4.22 (m, 1H), 2.48-2.34 (m, 2H), 2.31-2.16 (m, 3H), 2.09-1.98 (m, 1H) ppm; $^{13}$C NMR (100 MHz, CDCl$_3$) $δ_C$ 211.2, 48.1, 35.0, 33.9, 20.2 ppm; FT-IR $ν_{max}$ 1149 (s), 1741 (s), 2972 (w) cm$^{-1}$; GC-MS R$_t$ 2.88 min, m/z 164 [M]$^+$, 162 [M]$^+$, 83 [M-Br]$^+$.

Example 22. 2-Bromo-1-indanone (8b)

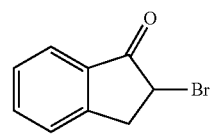

Chemical Formula: C₉H₇BrO

Pale yellow crystalline solid, m.p. 36-38° C. (petroleum ether), (lit. 37-38° C.), (1 mmol scale, 156 mg, 74%). $^1$H NMR (400 MHz, CDCl$_3$) δ 7.86 (d, J=7.7 Hz, 1H), 7.72-7.66 (m, 1H), 7.49-7.43 (m, 2H), 4.68 (dd, J=7.5, 3.2 Hz, 1H), 3.86 (dd, J=18.4, 7.7 Hz, 1H), 3.45 (dd, J=18.1, 3.0 Hz, 1H) ppm; $^{13}$C NMR (100 MHz, CDCl$_3$) $δ_C$ 199.6, 151.1, 136.0, 133.6, 128.3, 126.4, 125.1, 44.1, 38.0 ppm; FT-IR $ν_{max}$ 1208 (s), 1275 (s), 1460 (w), 1604 (m), 1717 (s) cm$^{-1}$; GC-MS R$_t$ 4.35 min, m/z 212 [M]$^+$, 210 [M]$^+$, 132 [M-Br]$^+$.

Example 23. 2-Bromo-2-methyl-2,3-dihydro-1H-inden-1-one (9b)

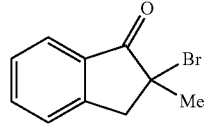

Chemical Formula: C₁₀H₉BrO

White crystalline solid, m.p. 70-71° C. (petroleum ether), (lit.71-72° C.), (1 mmol scale, 153 mg, 68%). $^1$H NMR (400 MHz, CDCl$_3$) δ 7.90 (d, J=7.6 Hz, 1H), 7.69 (td, J=7.5, 1.2 Hz, 1H), 7.50-7.43 (m, 2H), 3.82 (d, J=18.2 Hz, 1H), 3.51 (d, J=18.2 Hz, 1H), 1.99 (s, 3H) ppm; $^{13}$C NMR (100 MHz, CDCl$_3$) $δ_C$ 200.3, 149.1, 135.8, 132.7, 128.3, 126.3, 125.7, 59.5, 46.4, 26.8 ppm; FT-IR $ν_{max}$ 1045 (m), 1212 (m), 1286 (m), 1465 (m), 1605 (m), 1715 (s) cm$^{-1}$; GC-MS R$_t$ 4.27 min, m/z 226 [M]$^+$, 224 [M]$^+$, 145 [M-Br]$^+$.

Example 24. 3-Bromo-6-methylhept-5-en-2-one (11b)

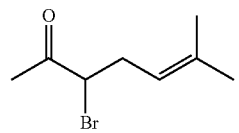

Chemical Formula: C₈H₁₃BrO

Brown liquid (1.25 mmol scale, 117 mg, 46%). $^1$H NMR (400 MHz, CDCl$_3$) δ 4.22 (dd, J=11.3, 1.5 Hz, 1H), 2.92-2.65 (m, 2H), 2.21 (s, 3H), 2.09-2.01 (m, 1H), 2.00 (s, 3H), 1.86 (s, 3H) ppm; $^{13}$C NMR (100 MHz, CDCl$_3$) $δ_C$ 207.3, 67.9, 66.1, 42.3, 35.0, 30.1, 29.9, 28.8 ppm; FT-IR $ν_{max}$ 1097 (s), 1370 (m), 1715 (s), 2977 (w) cm$^{-1}$; GC-MS R$_t$ 4.07 min, m/z 207 [M+H]$^+$, 205 [M+H]$^+$, 125 [M-Br]$^+$; ASAP-HRMS m/z found [M+H]$^+$ 205.0221, C₈H₁₄BrO requires 205.0228 (Δ=3.4 ppm).

Example 25. 1-Bromocyclohexanecarbaldehyde (12b)

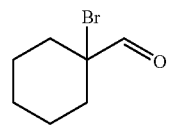

Chemical Formula: C₇H₁₁BrO

Brown liquid (1 mmol scale, 165 mg, 86%). $^1$H NMR (400 MHz, CDCl$_3$) δ 9.37 (s, 1H), 2.16-1.96 (m, 4H), 1.88-1.20 (m, 6H) ppm. $^{13}$C NMR (100 MHz, CDCl$_3$) $δ_C$ 192.8, 71.6, 34.4, 25.0, 23.2 ppm; FT-IR $ν_{max}$ 1723 (s), 2858 (w), 2936 (m) cm$^{-1}$; GC-MS R$_t$ 3.15 min, m/z 192 [M]$^+$, 190 [M]$^+$, 111 [M-Br]$^+$.

Example 26. 2-Hydroxy-2-phenylpropanal (13b)

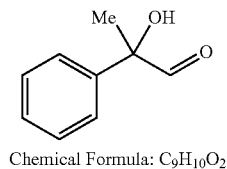

Chemical Formula: C$_9$H$_{10}$O$_2$

α-Bromo compound (2-bromo-2-phenylpropanal) underwent hydrolysis during purification. Pale yellow oil (1.1 mmol scale, 85 mg, 57%). $^1$H NMR (400 MHz, CDCl$_3$) δ 9.58 (s, 1H), 7.52-7.33 (m, 5H), 3.92 (br s, 1H), 1.73 (s, 3H) ppm; $^{13}$C NMR (100 MHz, CDCl$_3$) δ$_C$ 199.9, 139.2, 128.9, 128.2, 125.8, 79.1, 23.6 ppm; FT-IR ν$_{max}$ 697 (s), 1070 (m), 1729 (m), 2982 (m), 3451 (w, br) cm$^{-1}$; GC-MS R$_t$ 3.34 min, m/z 133 [M-OH]$^+$, 121 [M-CHO]$^+$.

Example 27. 2-Pentylphenol (14b)

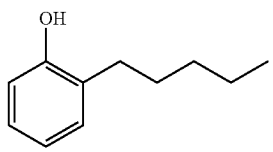

Chemical Formula: C$_{11}$H$_{16}$O

Colourless liquid (0.6 mmol scale, 42 mg, 42%). $^1$H NMR (400 MHz, CDCl$_3$) δ 7.16-7.07 (m, 2H), 6.89 (td, J=7.4, 1.2 Hz, 1H), 6.79 (dd, J=8.0, 1.2 Hz, 1H), 4.81 (s, 1H), 2.63 (m, 2H), 1.71-1.59 (m, 2H), 1.43-1.33 (m, 4H), 0.96-0.89 (m, 3H) ppm; $^{13}$C NMR (100 MHz, CDCl$_3$) δ$_C$ 153.4, 130.2, 128.6, 127.0, 120.8, 115.2, 31.7, 29.9, 29.5, 22.6, 14.1 ppm; FT-IR ν$_{max}$ 751 (s), 1218 (s), 1230 (s), 1367 (s), 1455 (s), 1740 (s), 2929 (m), 3430 (w, br) cm$^{-1}$; GC-MS R$_t$ 3.96 min, m/z 164 [M]$^+$, 107 [M-C$_4$H$_9$]$^+$, 77 [C$_6$H$_5$]$^+$.

Example 28. 2-Ethyl-1-phenylbutan-1-one (15a)

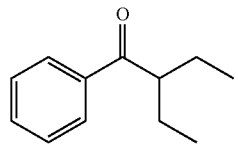

Chemical Formula: C$_{12}$H$_{16}$O

Prepared by diethylation of acetophenone. Colourless liquid (10 mmol scale, 650 mg, 37%). $^1$H NMR (400 MHz, CDCl$_3$) δ 8.01-7.97 (m, 2H), 7.61-7.55 (m, 1H), 7.52-7.46 (m, 2H), 3.33 (m, 1H), 1.89-1.54 (m, 4H), 0.90 (t, J=7.4 Hz, 6H) ppm; 13C NMR (100 MHz, CDCl$_3$) δ$_C$ 204.5, 137.8, 132.8, 128.6, 128.1, 49.2, 24.9, 11.9 ppm; FT-IR ν$_{max}$ 698 (s), 982 (m), 1214 (s), 1447 (s), 1677 (m), 2963 (m) cm$^{-1}$; GC-MS R$_t$ 3.85 min, m/z 176 [M]$^+$, 105 [M-C$_5$H$_{11}$]$^+$.

Example 29. 2-Bromo-2-ethyl-1-phenylbutan-1-one (15b)

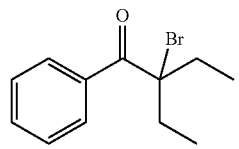

Chemical Formula: C$_{12}$H$_{15}$BrO

Yellow liquid obtained by reaction of 15a with CuBr$_2$ (2 equivalents) in MeCN (1.2 mmol scale, 179 mg, 58%). $^1$H NMR (400 MHz, CDCl$_3$) δ 8.07 (m, 2H), 7.58-7.38 (m, 3H), 2.32 (m, 4H), 0.97 (t, J=7.3 Hz, 6H) ppm; $^{13}$C NMR (100 MHz, CDCl$_3$) δ$_C$ 198.0, 136.6, 131.9, 129.4, 128.1, 73.2, 31.6, 9.7 ppm; FT-IR ν$_{max}$ 698 (s), 822 (m), 853 (m), 1229 (s), 1446 (m), 1674 (s), 2972 (w) cm$^{-1}$; GC-MS R$_t$ 4.46 min, m/z 175 [M-Br]$^+$, 105 [M-C$_5$H$_{11}$Br]$^+$; ASAP-HRMS: m/z found [M+H]$^+$ 255.0395, C$_{12}$H$_{16}$BrO requires 255.0385 (Δ=3.9 ppm).

Example 30. 1,2-Bis(4-methoxyphenyl)propan-1-one (16a)

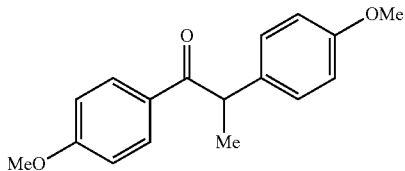

Chemical Formula: C$_{17}$H$_{18}$O$_3$

Prepared by α-methylation of desoxyanisoin. Thick yellow oil (10 mmol scale, 2.45 g, 91%). $^1$H NMR (400 MHz, CDCl$_3$) δ 7.99-7.94 (m, 2H), 7.24-7.19 (m, 2H), 6.90-6.82 (m, 4H), 4.62 (q, J=6.8 Hz, 1H), 3.84 (s, 3H), 3.78 (s, 3H), 1.51 (d, J=6.9 Hz, 3H) ppm; $^{13}$C NMR (100 MHz, CDCl$_3$) δ$_C$ 199.1, 163.1, 158.4, 134.0, 131.0, 129.5, 128.7, 114.3, 113.6, 55.4, 55.2, 46.6, 19.6 ppm; FT-IR ν$_{max}$ 780 (m), 832 (m), 952 (m), 1028 (m), 1165 (s), 1243 (s), 1509 (s), 1598 (s), 1671 (m), 2932 (w) cm$^{-1}$; GC-MS R$_t$ 6.00 min, m/z 270 [M]$^+$, 135 [MeOC$_6$H$_4$CO]$^+$+[MeOC$_6$H$_4$C$_2$H$_4$]$^+$.

Procedure for Catalytic Oxidation of 16a 1,2-Bis(4-methoxyphenyl)propan-1-one (16a), (163 mg, 0.6 mmol) was dissolved in MeCN (5 mL) in a microwave vial, the solution was degassed and then saturated with O$_2$. Copper(II) bromide (27 mg, 20 mol %) was then added and the vial was sealed. The solution was stirred at 85° C. under microwave irradiation for 132 h with 5 minutes of O$_2$ purging and monitoring by GC-MS at each of the following intervals; 24 h, 44 h, 62 h, 132 h. The solvent was then removed in vacuo and the product was isolated by SiO$_2$ column chromatography (8:2, hexane:EtOAc) as an orange oil (decomposition product (4-acetylanisole), 17) removed under high vacuum), (92 mg, 57%).

Example 31. 2-Bromo-, 2-bis(4-methoxyphenyl)propan-1-one (16b)

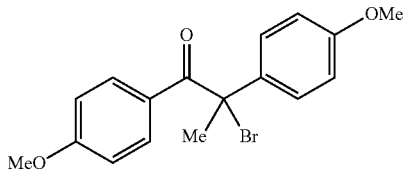

Chemical Formula: $C_{17}H_{17}BrO_3$

Inseparable from starting material (16a) and unsaturated product (16c) but observed in crude reaction mixture by ASAP-HRMS m/z found [M+H]+ 349.0436, $C_{17}H_{18}BrO_3$ requires 349.0439 (Δ=0.9 ppm).

Example 32. 1,2-Bis(4-methoxyphenyl)prop-2-en-1-one (16c)

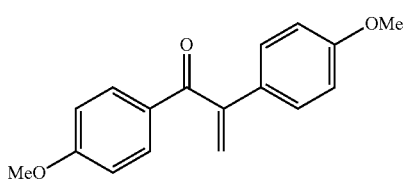

Chemical Formula: $C_{17}H_{16}O_3$

Orange oil (0.6 mmol scale, 92 mg, 57%), decomposition product removed in vacuo. $^1$H NMR (400 MHz, CDCl$_3$) δ 7.96-7.93 (m, 2H), 7.40-7.36 (m, 2H), 6.94-6.87 (m, 4H), 5.92 (s, 1H), 5.47 (s, 1H), 3.88 (s, 3H), 3.82 (s, 3H) ppm; $^{13}$C NMR (100 MHz, CDCl$_3$) δ$_C$ 196.7, 163.6, 159.7, 147.8, 132.4, 129.9, 129.7, 128.1, 117.0, 114.0, 113.6, 55.5, 55.3 ppm; FT-IR ν$_{max}$ 783 (m), 836 (m), 979 (m), 1027 (m), 1162 (s), 1250 (s), 1508 (s), 1595 (s), 1657 (m) cm$^{-1}$; GC-MS R$_t$ 6.30 min, m/z 268 [M]+, 135 [MeOC$_6$H$_4$CO]+, 133 [MeOC$_6$H$_4$C$_2$H$_2$]+.

All references cited herein are incorporated by reference in their entirety. The foregoing examples and description of certain preferred embodiments should be taken as illustrating, rather than as limiting, the present invention. As would be readily appreciated by a person skilled in the art, numerous variations and combinations of the features set forth above can be utilized without departing from the present invention, which are all encompassed by the present invention.

What is claimed is:

1. A method of preparing an α,β-unsaturated or α-bromo ketone or aldehyde, comprising oxidation of a corresponding acylated enol with copper(II) bromide (CuBr$_2$).

2. The method of claim 1, wherein the oxidation is conducted in a solvent selected from the group consisting of acetonitrile, lower alkyl alcohols, toluene, tetrahydrofuran, dimethyl sulfoxide, water, and combinations thereof.

3. The method of claim 2, wherein the solvent is acetonitrile, methanol, ethanol, isopropanol, water, or a combination thereof.

4. The method of claim 1, wherein the reaction is conducted at an elevated temperature.

5. The method of claim 1, wherein at least 0.1 equivalents of CuBr$_2$ are used.

6. The method of claim 1, characterized by equation (A), wherein the α,β-unsaturated ketone or aldehyde has a structure of formula (I), the α-bromo ketone or aldehyde has a structure of formula (II), and the corresponding acylated enol has a structure of formula (III):

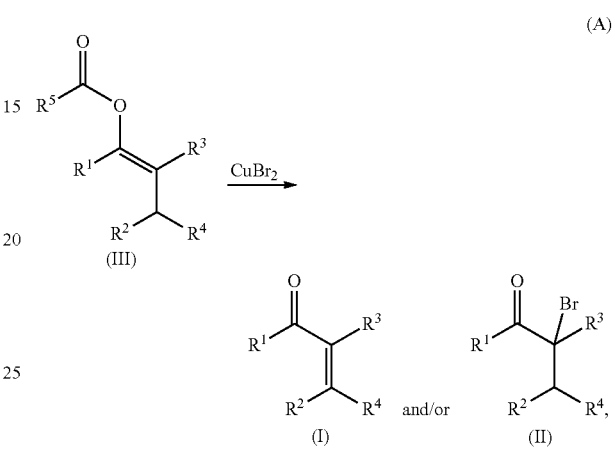

wherein:
R$^1$ and R$^2$ are each independently selected from the group consisting of hydrogen, C$_1$-C$_6$ alkyl, C$_6$-C$_{10}$ aryl, arylalkyl, C$_3$-C$_8$ cycloalkyl, and cycloalkylalkyl, each except hydrogen optionally substituted by one or more R$^y$ groups;
or alternatively R$^1$ and R$^2$ together form C$_2$-C$_5$ alkylene or 1,2-phenylene, each optionally substituted by one or more R$^y$ groups;
R$^3$ is selected from the group consisting of hydrogen, C$_1$-C$_{10}$ alkyl, C$_6$-C$_{10}$ aryl, arylalkyl, and —(CH$_2$)$_i$CO$_2$R$^z$, wherein i is 1, 2, or 3, and R$^z$ is C$_1$-C$_4$ alkyl;
R$^4$ is selected from the group consisting of hydrogen, C$_1$-C$_6$ alkyl, C$_6$-C$_{10}$ aryl, arylalkyl, and —(CH$_2$)$_j$CO$_2$R$^z$, wherein j is 0, 1, 2, or 3, and R$^z$ is C$_1$-C$_4$ alkyl;
or alternatively R$^3$ and R$^4$ together form a C$_3$-C$_5$ alkylene optionally substituted by one or more R$^y$ groups;
R$^5$ is selected from the group consisting of C$_1$-C$_6$ alkyl, C$_6$-C$_{10}$ aryl, arylalkyl, C$_3$-C$_8$ cycloalkyl, and cycloalkylalkyl; and
R$^y$ at each occurrence is independently selected from the group consisting of C$_1$-C$_6$ alkyl, C$_1$-C$_4$ haloalkyl, C$_1$-C$_4$ alkoxy, halo, and —(CH$_2$)$_k$CO$_2$R$^z$, wherein k is 0, 1, 2, or 3, and R$^z$ is C$_1$-C$_4$ alkyl.

7. The method of claim 6, wherein:
R$^1$ and R$^2$ together form a C$_2$-C$_3$ alkylene optionally substituted by one or more R$^y$ groups;
R$^y$ at each occurrence is independently selected from the group consisting of halogen, C$_1$-C$_6$ alkyl, C$_1$-C$_4$ haloalkyl, C$_1$-C$_4$ alkoxy, halo, and —(CH$_2$)$_k$CO$_2$R$^z$, wherein k is 0, 1, 2, or 3, and R$^z$ is C$_1$-C$_4$ alkyl;
R$^3$ is selected from the group consisting of hydrogen, C$_1$-C$_{10}$ alkyl, and arylalkyl;
R$^4$ is selected from the group consisting of hydrogen, C$_1$-C$_6$ alkyl, C$_6$-C$_{10}$ aryl, arylalkyl, C$_3$-C$_8$ cycloalkyl, cycloalkylalkyl, and —(CH$_2$)$_j$CO$_2$R$^z$, wherein j is 1, 2, or 3, and R$^z$ is C$_1$-C$_4$ alkyl; and
R$^5$ is methyl.

8. The method of claim 6, wherein $R^1$ and $R^2$ together form —$CH_2CH_2$— optionally substituted by one or two $R^y$ groups, characterized by equation (B):

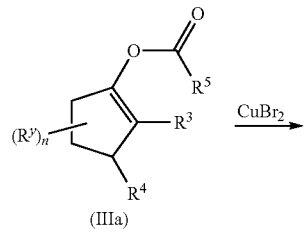

(B)

wherein:

n is 0, 1, or 2;

$R^3$ is hydrogen, $C_1$-$C_{10}$ alkyl, or arylalkyl;

$R^4$ is hydrogen, $C_1$-$C_6$ alkyl, or —$(CH_2)_jCO_2R^z$, wherein j is 1, 2, or 3, and $R^z$ is $C_1$-$C_4$ alkyl;

$R^5$ is methyl; and $R^y$ at each occurrence is independent selected from the group consisting of $C_1$-$C_6$ alkyl, $C_1$-$C_4$ haloalkyl, $C_1$-$C_4$ alkoxy, halo, and —$(CH_2)_kCO_2R^z$, wherein k is 0, 1, or 2, and $R^z$ is $C_1$-$C_4$ alkyl.

9. The method of claim 8, wherein n is 0; $R^3$ is hydrogen, $C_1$-$C_8$ alkyl, or benzyl; and $R^4$ is hydrogen, $C_1$-$C_4$ alkyl, or —$CH_2CO_2R^z$, wherein $R^z$ is methyl or ethyl.

10. The method of claim 6, wherein the α,β-unsaturated ketone is selected from the group consisting of:

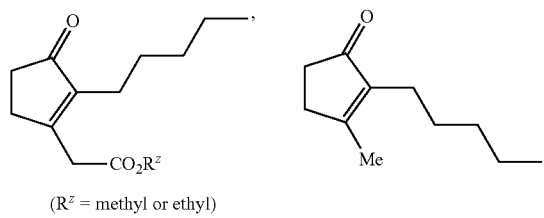

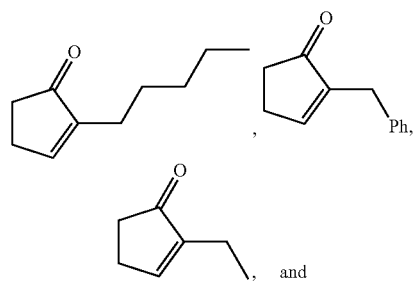

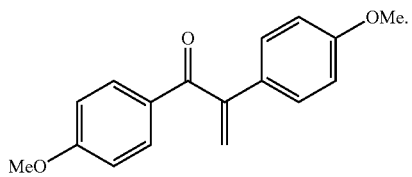

11. The method of claim 10, wherein the α,β-unsaturated ketone is dehydrohedione.

12. The method of claim 6, wherein the ca-bromo ketone or aldehyde is selected from the group consisting of:

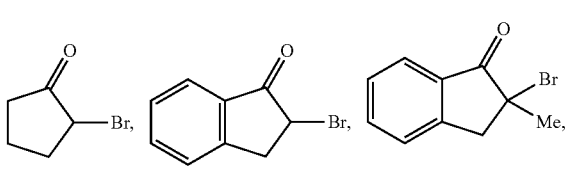

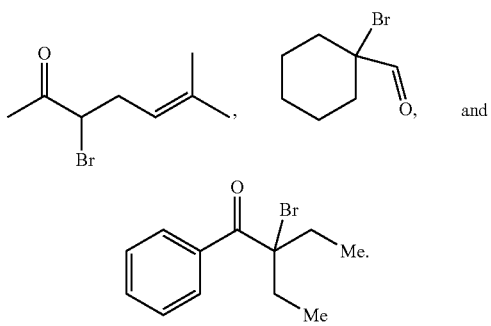

13. The method of claim 6, further comprising preparing the acylated enol intermediate by reacting a corresponding ketone or aldehyde with an acylating agent in the presence of an acid or base, characterized by equation (C):

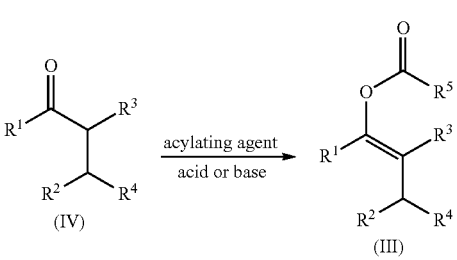

wherein each of $R^1$-$R^5$ is defined in claim 6.

14. The method of claim 13, wherein the acylating agent is acetic anhydride, acetyl chloride, or isopropenyl acetate; wherein the acid is an organic acid or a mineral acid; and wherein the base is an organic or inorganic base.

15. The method of claim 14, wherein the acylating agent is acetic anhydride or isopropenyl acetate, and the acid is a catalytic amount of p-toluenesulphonic acid.

16. A method of preparing a compound of formula Ib, characterized by equation (D):

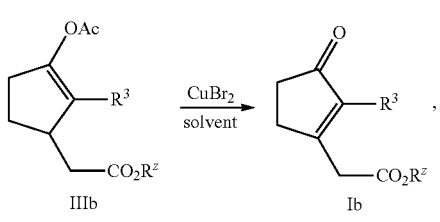

the method comprising reacting an enol acetate intermediate of formula IIIb with at least 1.5 equivalents of $CuBr_2$ in a solvent selected from acetonitrile and lower alkyl alcohols, or a combination thereof, at an elevated temperature until the compound of formula IIIb is substantially consumed; and isolating compound Ib from the reaction mixture, wherein $R^3$ is $C_1$-$C_5$ alkyl, and $R^z$ is $C_1$-$C_4$ alkyl.

17. The method of claim 16, further comprising preparing the enol acetate intermediate IIIb by reacting a compound of formula IVb with isopropenyl acetate in the presence of p-toluenesulphonic acid (p-TSA), characterized by equation (E):

wherein $R^3$ is $C_1$-$C_8$ alkyl, and $R^z$ is $C_1$-$C_4$ alkyl.

18. The method of claim 17, wherein the amount of pTSA is about 0.1 to about 0.5 equivalents relative to the compound of IVb.

19. The method of claim 16, wherein $R^3$ is $C_2$-$C_6$ alkyl, and $R^z$ is methyl or ethyl.

20. The method of claim 16, wherein $R^3$ is 1-pentyl, and $R^z$ is methyl, the amount of $CuBr_2$ is about 2 equivalents, the solvent is acetonitrile or methanol, and the elevated temperature is reflux temperature.

* * * * *